(12) United States Patent
El-Tanani et al.

(10) Patent No.: US 8,609,332 B2
(45) Date of Patent: Dec. 17, 2013

(54) ASSAY

(75) Inventors: Mohamed K. El-Tanani, Belfast (GB); Patrick Gerard Johnston, Belfast (GB)

(73) Assignee: Queen's University of Belfast, Belfast (GB)

( * ) Notice: Subject to any disclaimer, the term of this patent is extended or adjusted under 35 U.S.C. 154(b) by 549 days.

(21) Appl. No.: 12/311,192

(22) PCT Filed: Sep. 20, 2007

(86) PCT No.: PCT/GB2007/003599
§ 371 (c)(1),
(2), (4) Date: Apr. 27, 2009

(87) PCT Pub. No.: WO2008/035096
PCT Pub. Date: Mar. 27, 2008

(65) Prior Publication Data
US 2009/0312395 A1    Dec. 17, 2009

(30) Foreign Application Priority Data

Sep. 20, 2006  (GB) .................................. 0618486.5
Dec. 20, 2006  (GB) .................................. 0625379.3

(51) Int. Cl.
*C12Q 1/68* (2006.01)

(52) U.S. Cl.
USPC .............................. 435/6; 435/325; 435/375

(58) Field of Classification Search
None
See application file for complete search history.

(56) References Cited

U.S. PATENT DOCUMENTS

| 6,613,534 B2 * | 9/2003 | Setaluri et al. | 435/7.23 |
| 7,521,195 B1 * | 4/2009 | Joseloff et al. | 435/7.1 |

FOREIGN PATENT DOCUMENTS

| WO | WO 2004/055519 | 7/2004 | ............. G01N 33/68 |
| WO | WO 2005/032495 | 4/2005 | |

OTHER PUBLICATIONS

Hao, X. et al: "Differential gene and protein expression in primary breast malignancies and their lymph node metastases as revealed by combined cDNA microarray and tissue microarray analysis," *American Cancer Society*, (2005), 100(6) 1110-1122.

Seewald, M. J. et al: "Biochemical characterization of the Ran-RanBPI-RanGAP system: Are RanBP proteins and the acidic tail of RanGAP required for the Ran-RanGAP GTPase reaction?" *Molecular and Cellular Biology, American Society for Microbiology*, (2003), 23(22) 8124-8136.

* cited by examiner

*Primary Examiner* — Kimberly Chong
(74) *Attorney, Agent, or Firm* — Drinker Biddle & Reath LLP

(57) ABSTRACT

RAN and RAN Binding Protein 1 have been determined to be markers of invasive and metastatic potential of a tumour cell. There is described methods and kits for the detection of the level of RAN and RAN Binding Protein 1 and the use thereof.

4 Claims, 11 Drawing Sheets

Figure 1C:
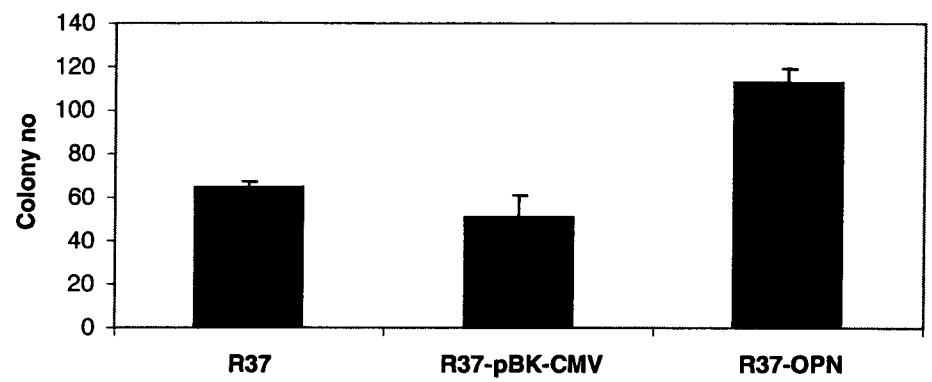

Figure 1
Fig.1A
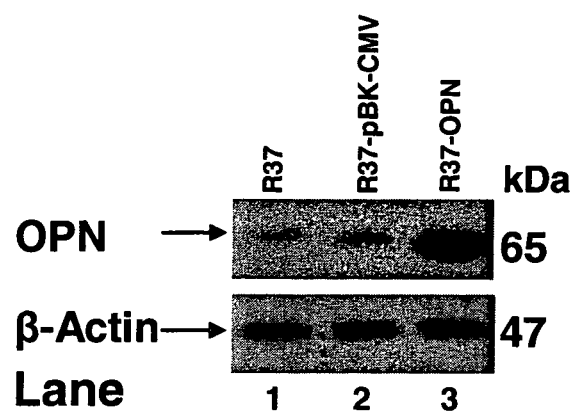
Fig.1B
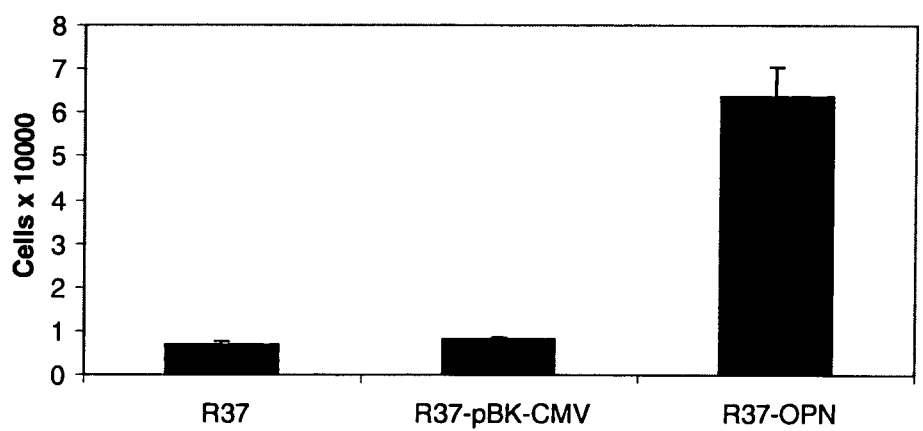

Figure 2
Fig.2A
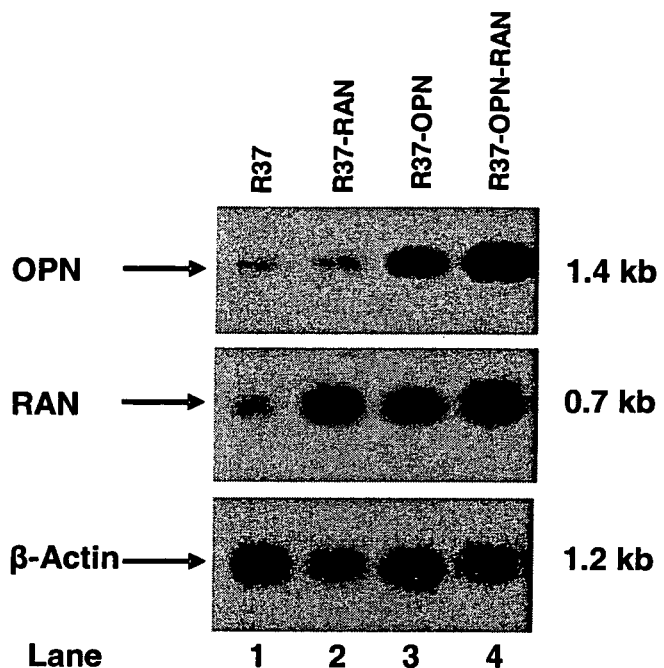
Fig.2B
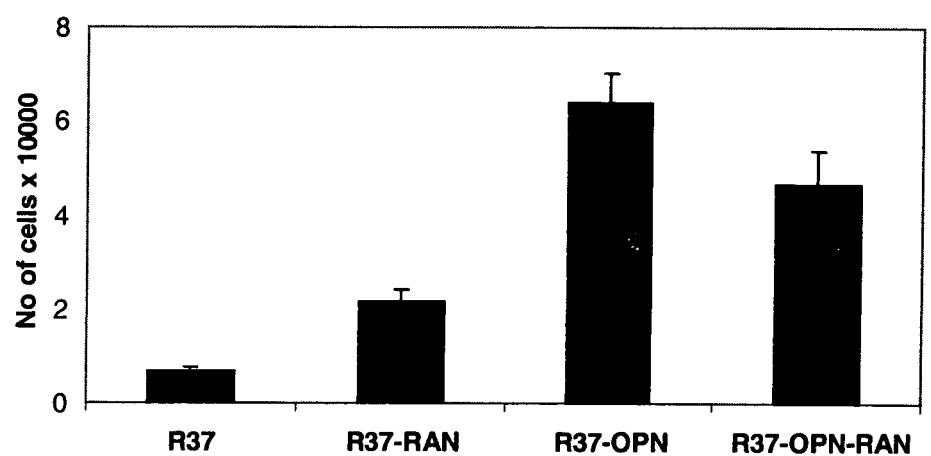

Figure 3
Fig.3A
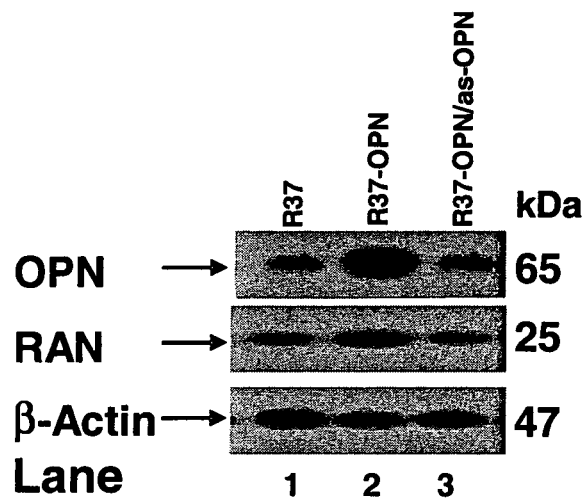
Fig.3B
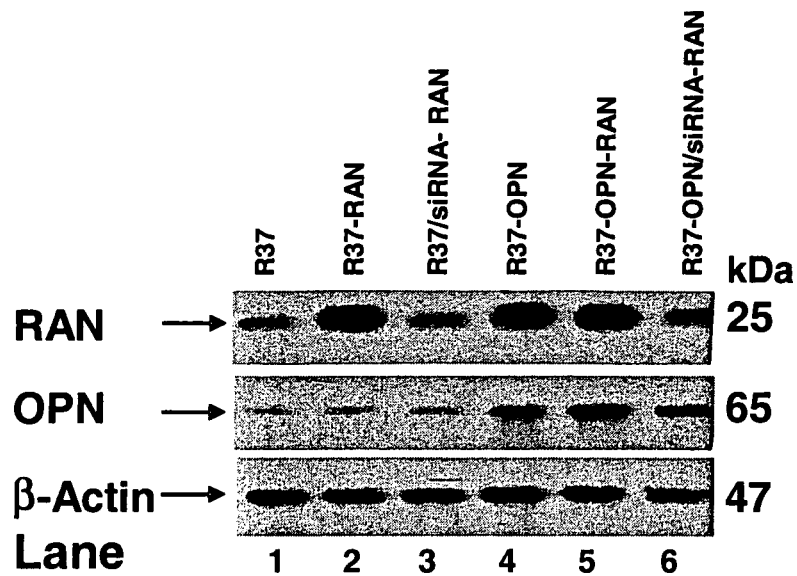

Figure 4
Fig 4A
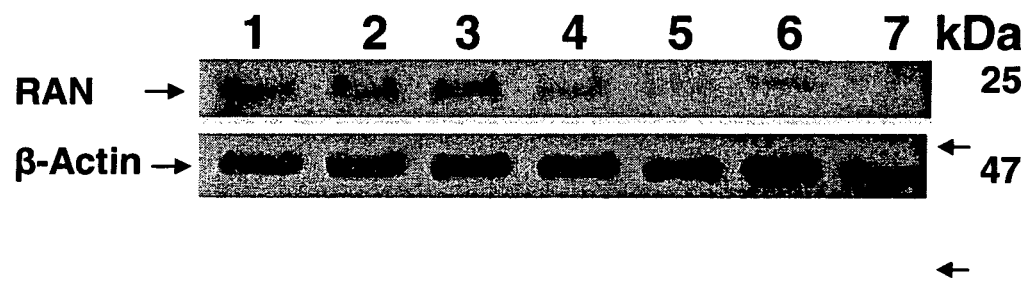
Fig 4B
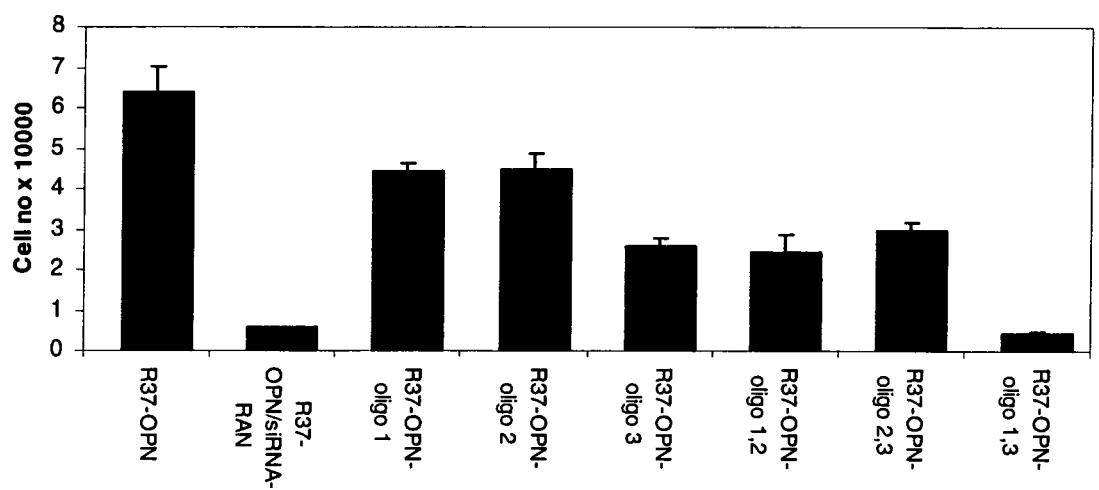

Figure 5
Fig.5A
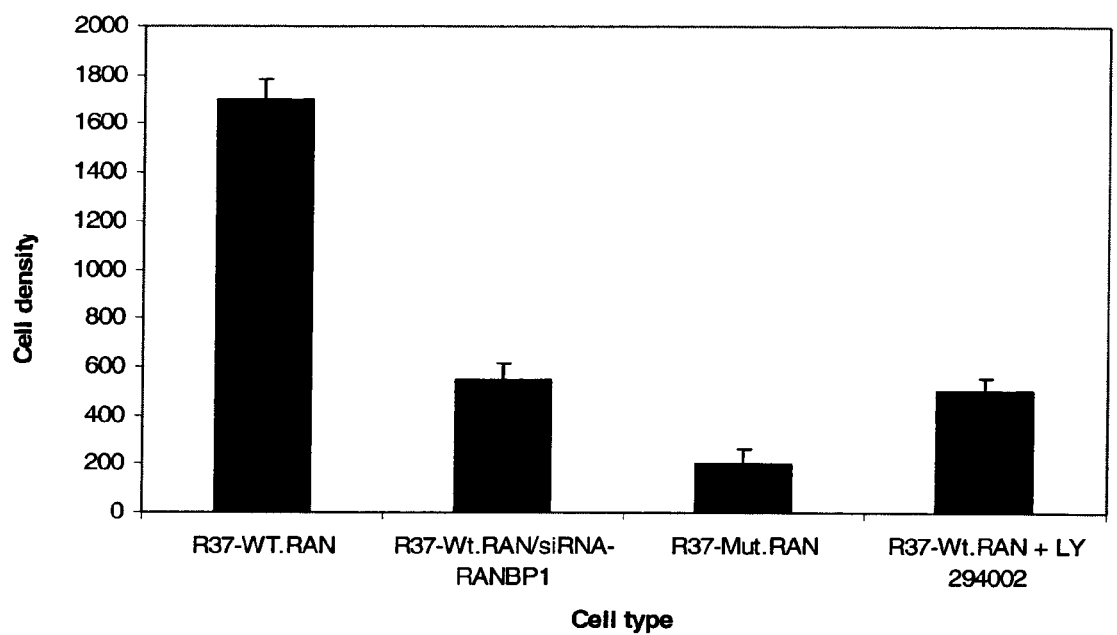
Fig.5B
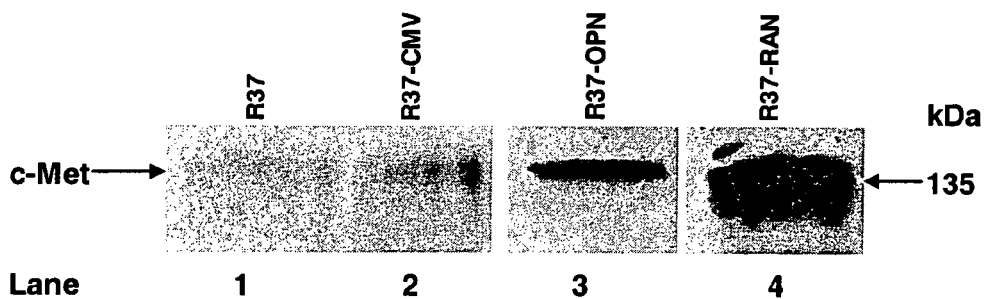

ASSAY

FIELD OF THE INVENTION

An assay for identifying a modulating agent of OPN mediated cell malignant transformation and/or OPN signalling pathway.

BACKGROUND OF THE INVENTION

Metastasis is the major cause of treatment failure in various type of cancer and particularly in breast cancer patients. The extracellular matrix glycophosphoprotein osteopontin (OPN) is normally secreted by osteoblasts and is utilised as an extracellular adhesion molecule. Osteopontin has also been associated with certain aspects of malignant transformation (1) by enhancing malignant cell attachment and migration and contributing to anchorage-independent growth of tumour cells (2, 3). Transfection of benign, non-metastatic rat mammary cells with cDNA for OPN has been determined to endow the transfectants with the ability to overproduce OPN in vitro and to metastatsize in vivo (4). OPN overexpression has been associated with poor prognosis in human primary breast cancer (5, 6) and OPN has been shown to be the single most powerful prognostic factor in a multivariate analysis against outcome, in a large prospective study of breast cancer patients (7). Although it is known that circulating plasma levels of OPN are higher in metastatic breast cancer patients (8), the precise molecular mechanisms of OPN regulated metastasis remains unclear.

SUMMARY OF THE INVENTION

RAN GTPase (RAN) is a small GTP (Guanosine triphosphate) binding protein of the RAS superfamily. RAN has been determined to be essential for the translocation of RNA and proteins through the nuclear pore complex. A direct association between RAN and viral oncoproteins such as human adenovirus E1A, human papilloma virus E7 and SV40 large T antigen has been reported to be closely associated with cellular transformation and genomic instability induced by viral infection (27) and RAN GTPase has been determined to be highly expressed in most of the adenocarcinoma and squamous cell carcinoma cell lines tested from various organs, including the stomach, lungs, head and neck, pancreas and colon and also in metastatic tumour cells (29), but not in the normal cells in those tumour tissues (28). RAN has also been determined to regulate spindle cell cycle progression and DNA synthesis (26).

Whilst RAN has been determined to be associated with uncontrolled cell growth, determining cell growth does not give a measure of the process of metastasis, which is a largely independent process.

By analysing gene expression between the benign rat mammary cell line Rama 37 (R37) and R37 cells stably transfected with an expression vector for OPN, termed R37-OPN cells, wherein the former cells produce low levels of OPN and are non-invasive and nonmetastatic (9), while the latter cells produce high levels of OPN and are invasive, the inventors have determined that RAN has a further role in invasion and metastasis and that RAN and RAN Binding Protein 1 have substantially increased expression in association with OPN.

According to a first aspect of the present invention there is provided a method of determining whether a tumour cell has invasive/metastatic potential comprising the steps:

determining the level of a marker in a tumour cell from a sample, wherein the marker is at least one member selected from the group comprising RAN, RAN Binding Protein 1 and a derivative thereof, and comparing the level of the marker detected in said tumour cell with the level determined for the marker in a non-invasive and/or non-metastatic tumour cell, wherein an increase in the level of the marker in the tumour cell from the sample is indicative that the tumour cell has invasive and/or metastatic potential.

Suitably, the sample may be tissue or cells from a subject. In embodiments, the sample may be isolated from the subject, the tumour cell may be isolated from the sample and/or the contents of the cell, for example mRNA, or proteins, may be isolated before the level of the marker is determined. In embodiments, the level of the marker in an invasive and/or metastatic tumour cell is at least 4 times, at least 5 times, at least 6 times, at least 7 times, at least 8 times, at least 9 times, the level of the marker in a non-invasive and/or metastatic cell.

By invasive and/or metastatic potential it is meant that the tumour cell is invasive and/or metastatic or is progressing towards being invasive and/or metastatic.

As will be appreciated, this method may be used to determine whether a subject is afflicted with an invasive/metastatic tumour.

Accordingly, there is provided a second aspect of the invention to assess whether a subject is afflicted with an invasive/metastatic tumour comprising the steps:

determining the level of a marker in a tumour cell from a sample from a subject, wherein the marker is at least one member selected from the group comprising RAN, RAN Binding Protein 1 and a derivative thereof, and comparing the level of the marker detected in said tumour cell with the level determined for the marker in a non-invasive and/or non-metastatic tumour cell, wherein an increase in the level of the marker in the tumour cell from the sample is indicative that the subject is afflicted with a tumour which has invasive/metastatic potential.

In addition to allowing the invasive and/or metastatic potential of a tumour cell to be measured at a single time point, the present invention provides for the measurement of invasive and/or metastatic potential of a tumour cell(s) at multiple time points.

Accordingly, a third aspect of the present invention provides a method for monitoring a tumour cell to determine the invasive and/or metastatic potential of said tumour cell, the method comprising the steps of:

a) detecting in the tumour cell at a first time point, the level of a marker, wherein the marker is at least one member selected from the group comprising RAN, RAN Binding Protein 1 and a derivative thereof, b) repeating step a) at a subsequent point in time; and c) comparing the level of a marker in steps a) and b) wherein an increase in the level of marker from a first time point to a subsequent time point is indicative that the tumour cell is gaining invasive and/or metastatic potential.

In the period between the first time point and a subsequent time point, a test agent can be applied to the tumour cell to determine if the level of marker is affected by said test agent. In particular embodiments the tumour cell can be subjected to a particular condition, for example radiation, surgery or the like in the period between the detection of the level of the marker at the first time point and the detection at a subsequent time point.

Accordingly, a fourth aspect of the present invention provides a method for monitoring the progression of a cancer in a subject comprising the steps of:
   a) detecting, in a sample of a tumour from a subject, at a first time point, the level of a marker, wherein the marker is at least one member selected from the group comprising RAN, RAN Binding Protein 1 and a derivative thereof,
   b) repeating step a) at a subsequent point in time; and
   c) comparing the level of a marker in steps a) and b) wherein an increase in the level of marker from a first time point to a subsequent time point is indicative that the tumour cell is gaining invasive and/or metastatic potential and therefrom that the cancer is progressing in the subject.

A therapy, for example a drug treatment, surgical intervention or the like may be provided to the subject between the first time point and the subsequent point in time and the method will provide an indication as to whether the therapy is having a beneficial affect on the subject, (whether the cancer is gaining invasive and/or metastatic potential).

In circumstances wherein the therapy is a test agent or composition, it will be appreciated that the invention provides a method by which the ability of different test agents to affect invasion and/or metastasis can be assessed.

Accordingly a fifth aspect of the present invention provides a method to select an agent to inhibit invasion and/or metastasis by a tumour cell in a sample, the method comprising the steps:
   providing at least first and second aliquots, wherein each aliquot comprises at least one tumour cell, from the sample;
   exposing a first aliquot of the sample to a first test agent;
   exposing a second aliquot of the sample to a second test agent;
   optionally, exposing a further aliquot of the sample to a further respective test agent;
   determining the level of a marker from a tumour cell of each aliquot, wherein the marker is at least one member selected from the group comprising RAN, RAN Binding Protein 1 and a derivative thereof,
   comparing the level of the marker detected in each of the aliquots, and
   selecting the agent which provides for a lower level of marker in an aliquot with that agent relative to the other agents.

Should a portion of a tumour remain the body of a subject, the selection of an agent which provides a lower level of marker in an aliquot with that agent relative to other agents can be utilised to provide a medicament to the subject.

Accordingly, a sixth aspect of the present invention provides a method for inhibiting invasion or metastasis of a tumour in a subject, the method comprising the steps:
   providing a sample from a tumour of a subject;
   providing at least first and second aliquots, wherein each aliquot comprises at least one tumour cell, from the sample;
   exposing a first aliquot of the sample to a first test agent;
   exposing a second aliquot of the sample to a second test agent;
   optionally, exposing a further aliquot of the sample to a further respective test agent;
   determining the level of a marker from a tumour cell of each aliquot, wherein the marker is at least one member selected from the group comprising RAN, RAN Binding Protein 1 and a derivative thereof,
   comparing the level of the marker detected in each of the aliquots,
   selecting the agent which provides for a lower level of marker in an aliquot with that agent relative to the other agents, and
   administering to the subject a therapeutically effective amount of at least one agent which provides for a lower level of marker in an aliquot with that agent relative to the other agents.

The present inventors have determined agents which reduce the level of RAN protein and/or RAN Binding Protein 1 present in a tumour and which would thus decrease the invasion and/or metastatic potential of a tumour cell.

Suitably such an agent may be an antibody with binding specificity to RAN (SEQ ID NO 1) or RAN Binding Protein 1 (SEQ ID NO 3) or a derivative thereof.

Suitably such an agent may be a nucleic acid complementary to a polynucleotide which encodes RAN (SEQ ID NO 1) or RAN Binding Protein 1 (SEQ ID NO 3) or a fragment of a polynucleotide which encodes RAN or RAN Binding Protein 1.

In one embodiment, the expression or activity of RAN, RAN Binding Protein 1 or derivatives thereof are blocked.

In particular embodiments, the method is used to treat tumours or subjects with tumours which are invasive and/or are metastatic. In particular embodiments the tumours can be cancerous cells from the stomach, the lungs, the head and neck, the pancreas and the colon, the bladder or the breast. In particular embodiments the tumours can be cancerous cells from the colon, bladder or breast. In specific embodiments the cancerous cells can be from breast tissue.

A nucleic acid of the present invention may be a molecule which can hydrogen bond to and anneal with a polynucleotide sequence which encodes RAN (SEQ ID NO 1) or RAN Binding Protein 1 (SEQ ID NO 3). An antisense nucleic acid of the present invention may be complementary to the entire coding strand, a portion thereof, for example all or part of the protein coding region, or all or part of a non-coding region (5' and 3' sequences which flank the coding region and are not translated into amino acids) of the coding strand. In particular embodiments an antisense nucleic acid can be about 5, 10, 15, 20, 25, 30, 35, 40, 45, or 50 or more nucleotides in length. An antisense nucleic acid may be synthetically synthesised and may include modified nucleotides to enhance the stability of the antisense molecule or the duplex formed by the antisense molecule and the nucleotide sequence to which it binds.

In particular embodiments, the method comprises providing a subject with an antisense nucleic acid or polynucleotide using a vector that expresses the antisense nucleic acid in tumour cells. Administration of antisense nucleic acid may be by, for example, direct injection into the tumour, via infusion of the antisense systemically into the body or delivery to a target site using a vector. As will be appreciated by those of skill in the art, various targeting means, for example peptide and/or antibody conjugates and/or expression systems may be used to target a genetic polynucleotide sequence.

The invention also encompasses ribozymes with specificity to polynucleotide sequences which encode RAN or RAN Binding Protein 1, nucleic acids which form triple helical structures to polynucleotide sequences which encode RAN or RAN Binding Protein 1 or dsRNA which can bind polynucleotide sequences which encode RAN or RAN Binding Protein 1.

In particular embodiments the nucleic acid sequences can be selected from SEQ ID NO 5, SEQ ID NO 6, SEQ ID NO 7, SEQ ID NO 8, SEQ ID NO 9, or SEQ ID NO 10.

In addition to determining agents which cause a decrease in the levels of a marker, the present invention also provides a method for determining agents, (test compounds) which increase the level of RAN and/or RAN Binding Protein 1 or effect the activity of RAN and/or RAN Binding Protein.

According to a seventh aspect of the present invention there is provided a method for identifying a modulating agent of OPN-mediated cell malignant transformation, said method comprising the steps of:
providing an assay comprising at least one member selected from the group comprising RAN, RAN Binding Protein 1 and a derivative thereof,
contacting a modulating agent candidate with said assay under suitable conditions; and
detecting a variation in the activity of the assay by comparing the assay's activity without said candidate with the assay's activity in presence of said candidate.

Suitably a modulating candidate agent may include, but is not limited to an antibody, a peptide, a hormone, a nucleic acid, an oligonucleotide, natural or synthetic compounds or small molecules.

Preferably, the contacting step is followed by an incubating step wherein the mixture obtained in the contacting step is incubated for a time period and under conditions suitable to allow interaction between the components and/or the test substance.

In embodiments of the invention at least one member selected from the group comprising RAN, RAN Binding Protein 1 and a derivative thereof may be immobilised, for example by being bound to a solid surface of a compartment of a kit.

In a specific embodiment, the method for identifying a modulating agent of OPN-mediated cell malignant transformation can be performed by maintaining Rama 37 and its subclones and breast cancer cells MDA-MB-231 and MDA-MB 435S, which may be obtained from the American Type Culture Collection (Rockville, Md.), in a humidified atmosphere of 95% (v/v) air and 5% (v/v) $CO_2$ at 37° C. in routine medium (RM) (Dulbecco's Modified Eagles Medium (DMEM) (Sigma, Poole, UK) containing 10% (v/v) foetal calf serum (FCS), 100 µg/ml penicillin and 100 µg/ml streptomycin (Gibco BRL, Paisley, UK). Prior to treatment with a candidate modulating agent the cells can be grown overnight in routine media. The next day the candidate modulating agent can be added at a range of different concentrations in routine media unless otherwise specified. Cells are typically treated for 48 hours prior to assaying using for example, but not limited to western blotting for RAN, RANBP1 and/or OPN proteins, cell growth assays, cell adhesion assays, soft-agar assays, or matrigel Invasion assays as described herein.

In particular embodiments of the method, cell growth assays may be carried out by plating out $1 \times 10^5$ cells in one well of a six well plate. At time points of 3, 6, 12, 24, 48, 72 and 96 hours cells may be removed by trypsination and counted using a haemocytometer. Typically assays are carried out in triplicate to allow statistical analysis.

The contacting (eventually incubating) step may advantageously be followed by a removal step wherein any unassociated candidate is removed from the mixture.

Detection of the variation of the activity can be conducted by any convenient means. Generally detection may be via an antibody, for example a monoclonal antibody, the presence of which is established by exposure to a second labelled monoclonal antibody in a typical ELISA-style assay. Alternatively, the candidate may be labelled (e.g. radioactively, fluorescently or enzymatically) to determine its binding to the other component.

The assay described above can also be used to study cellular biological aspects of the osteopontin signal transduction pathway which would allow progress in the understanding of tissue invasion of cancer and more particularly epithelial tissues such as breast cancer and may provide new potential drug targets.

It is preferred that that the assay be a cellular assay which may comprise cultured cells of a transformant cell line. Such a cell line may be the result of the transfection of a cell line with an expression vector comprising the sequence or a substantial portion of the sequence a RAN polynucleotide sequence and/or RANBP1 polynucleotide. In particular embodiments the transformant cell line can overexpress the corresponding RAN polypeptide and/or RANBP1 polypeptide. The transformant cell line can be further transfected by an expression vector comprising the sequence of a substantial portion of the sequence of OPN nucleotide sequence. Preferably, the RAN, RANBP1 and optionally the OPN, nucleotide sequence(s) are human sequences.

Alternatively, the cells may be from a tumour sample.

Suitably, the agents determined by the invention, for example the modulating agents determined by the above assay, may be useful in therapeutic or diagnostic uses. It is understood that the amount of an agent determined by the methods of the present invention provided to a subject would depend upon a number of factors within the knowledge of a skilled physician, veterinarian or researcher. The dose of such an agent will vary, for example, depending on the identity, size, condition of the subject being treated and the route of administration. Suitably, an agent may be administered to a subject in a pharmaceutical composition. Pharmaceutical compositions may be formulated to be compatible with its intended route of administration, for example, intravenous, intradermal, subcutaneous, oral, transdermal, transmucosal, and rectal administration.

According to an eighth aspect of the present invention there is provided a method to assess the potential of a test agent to cause invasion and/or metastasis by a tumour cell comprising:
providing at least first and second aliquots, wherein each aliquot comprises at least one tumour cell, from the sample,
exposing a first aliquot of the sample to a first test agent,
determining the level of a marker from a tumour cell of each aliquot, wherein the marker is at least one member selected from the group comprising RAN, RAN Binding Protein 1 and a derivative thereof, and
comparing the level of the marker detected in each of the aliquots,
wherein a significantly increased level of a marker in the aliquot exposed to the test agent, relative to the aliquot not exposed to the test agent is indicative that the test agent has invasive and/or metastatic potential.

It may be advantageous to provide/administer such a test agent to a subject and accordingly, a further aspect of the present invention is the administration of such an agent to a subject.

The present invention further relates to kits.

According to a ninth aspect of the present invention, there is provided a kit to assess whether a tumour cell is invasive and/or metastatic, the kit comprising a reagent for assessing the level of marker in a tumour cell, wherein the marker is at least one member selected from the group comprising RAN, RAN Binding Protein 1 and a derivative thereof.

In an embodiment of a kit, the reagent can be an antibody with binding specificity for RAN, RAN Binding Protein 1 or a derivative thereof. Suitably, the reagent may be employed for in situ histological detection of RAN, RAN Binding Protein 1 or a derivative thereof. As will be appreciated, in situ detection may comprise, applying the reagent to a sample removed from a subject and then using a second labelled antibody to visualise binding of the reagent. Such a procedure allows determination of the presence of RAN, RAN Binding Protein 1 or a derivative thereof and also distribution in the sample.

Alternatively, in other embodiments, labelled nucleic acid probes may be used to detect mRNA or RAN or RAN Binding Protein 1.

According to a tenth aspect of the present invention, there is provided a kit for assessing an agent for inhibiting invasion and/or metastasis by a tumour cell, the kit comprising:
a) a plurality of test compounds, and
b) a reagent for assessing the level of marker in a tumour cell, wherein the marker is at least one member selected from the group comprising RAN, RAN Binding Protein 1 and a derivative thereof.

Suitably, a kit may comprise a visual indicator of the reagent, for example, a labelled antibody capable of binding to the reagent or able to the reagent and a marker complex.

A kit of the invention may, optionally, comprise liquids, for example buffers suitable for detecting the level of marker in a sample, for example, buffers which provide for the stringent hybridisation of a reference nucleotide to a nucleotide sequence of a marker, buffers which provide for binding of an antibody specific to a marker protein, and the like. Optionally, a kit can comprise instructional material describing the way in which a method of the invention should be performed and/or a compartment(s) for samples.

According to the invention, the level of expression of a marker of the invention, wherein the marker is at least one member selected from the group comprising RAN, RAN Binding Protein 1 and a derivative thereof, can be determined by detecting the presence of
  a) the marker protein having the amino acid sequence SEQ ID NO 1 or the marker protein having the amino acid sequence SEQ ID NO 3 or a fragment of said sequences using a reagent with binding specificity to at least one of said amino acid sequences or fragments thereof, for example said reagents can include an antibody, an antibody derivative, an antibody fragment or a single chain antibody;
  b) the nucleotide transcripts which encode one of the amino acid sequence SEQ ID NO 1 or SEQ ID NO 3 such as SEQ ID NO 2 or SEQ ID NO 4 or a fragment thereof, or
  c) a metabolite or other peptide which is produced directly or indirectly by one of the marker proteins.

Whilst not wishing to be bound by theory, mechanistically the inventors have determined that RAN increases Met receptor and Akt phosphorylation (FIG. 5) and that the phosphoinositol 3 kinase (PI3K) inhibitor LY294002 or mutation of RAN in the GTP binding pocket blocks RAN mediated invasion of R37 cells by about 70% and 82%, respectively (FIG. 5A). LY294002 at the concentrations used, is specific for inhibition of P13K. The inventors also consider that cell surface receptors linked to PI3K may mediate such effects, one such receptor being c-Met.

By the term "indicative", there may be at least a 10%, more preferably a 20%, more preferably a 30%, more preferably a 50%, and most preferably a 90% likelihood that the tumour cell is invasive and/or metastatic.

An increased level of the marker in the tumour cell of the sample may be at least a two-fold, at least three-fold, at least five-fold, at least seven fold, at least ten-fold, at least one-hundred-fold or at least five-hundred fold more than the level of marker present in a non-invasive and/or metastatic tumour cell. The level of marker present in a non-invasive and/or non metastatic tumour may be determined by assessing the level of marker in a sample from archived subject samples or the like.

In embodiments, the level of marker can be compared with an absolute amount or concentration of the marker from a standard reference sample.

In an embodiment of the method the level of the marker is determined by detecting a transcribed polynucleotide or portion thereof which encodes RAN or RAN Binding Protein 1.

In embodiments of the method, the transcribed polynucleotide is mRNA. In other embodiments, the transcribed polynucleotide is cDNA. Suitably, the transcribed polynucleotide can be amplified, for example using Polymerase Chain Reaction (PCR) or RT-PCR. In particular embodiments of the invention, the level of a marker is determined by detecting the binding of a reference nucleotide sequence which can bind to a transcribed polynucleotide or a portion thereof under stringent hybridisation conditions.

The reference polynucleotide may be bound to a solid substrate or be labelled with, for example, a chromophore, a fluorophore, an enzyme, or enzyme co-factor to allow detection of hybridisation. Polymerase Chain Reaction can, optionally, be used to amplify cDNA before hybridisation to a reference polynucleotide. In alternative embodiments, PCR or other techniques, for example single nucleotide polymorphisms, can be used to measure the level of marker present.

In alternative embodiments the level of the marker is determined by detecting the presence of RAN protein or RAN Binding Protein 1 or a fragment thereof. Suitably, the presence of protein is detected using a reagent which specifically binds to the protein. In embodiments of the invention, the reagent is selected from an antibody, an antibody derivative, or an antibody fragment. In particular embodiments, an antibody used to measure the level of marker can be labelled with, for example, a radio-label, a fluorophore-label or an enzyme-label, an antibody derivative can be conjugated with a substrate or ligand and an antibody fragment can be, for example a single chain antibody or an isolated antibody hypervariable domain.

In embodiments the tumour cell may be from various organs and tissues, including the stomach, lungs, head and neck, pancreas and colon and also the bladder and the breast. In particular embodiments the tumour cell is from the breast.

Preferred features and embodiments of each aspect of the invention are as for each of the other aspects mutatis mutandis unless context demands otherwise.

Embodiments of the present invention will now be described, by way of example only, with reference to the accompanying drawings in which:

FIG. 1A—A Northern (upper panel) and immuno (lower panel) blot showing OPN mRNA and protein levels in R37, R37-pBK-CMV and R37-OPN cells. Cell lysates were diluted and 20 μg loaded onto a SDS 10% (w/w) polyacrylamide gel as follows: lane 1 R37, lane 2, R37-pBK-CMV, lane 3 R37-OPN and specific proteins were detected using antibodies to OPN and β-actin. Bands were quantified using densitometric analysis and normalized against β-actin. The average fold increase for three different experiments are: lane 1=1, lane 2=1±0.2 and lane 3=10±1.7.

FIG. 1B—The ability of transfected cell lines to adhere to a laminin-treated surface was assessed over a 30 min period and the number of adherent cells quantified. Results of the mean±standard errors from three independent experiments are shown.

FIG. 1C—A soft agar assay was carried out to assess the ability of stable transfected cell lines to grow in an anchorage independent environment. The colony number was assessed after 5 days. Empty vector pBK-CMV had no effect on anchorage independent cell growth. Results of the mean±standard errors from three independent experiments are shown.

Figure 1D:
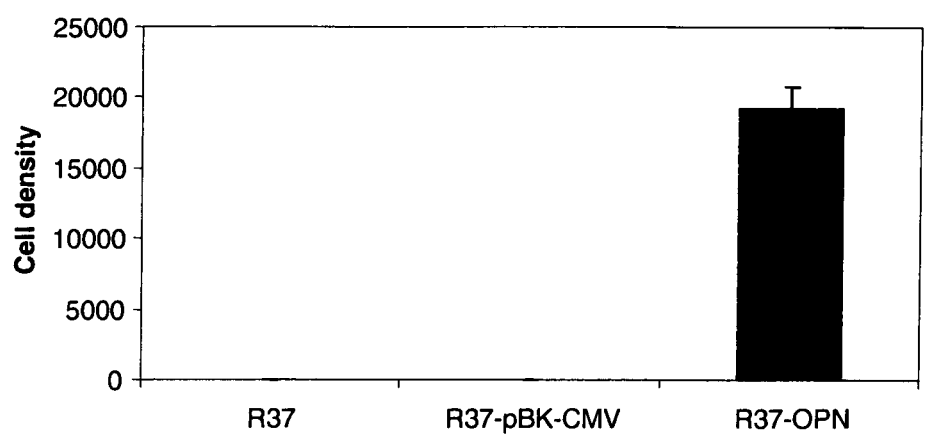

FIG. 1D—R37 and R37-OPN were plated on ECM-coated filters (500 µg/ml) in Boyden chambers. The number of cells that migrated through the filter after 48 hrs was determined by staining and scanning using a digital imaging system (Experimental procedures). Results of the mean±standard errors from three independent experiments are shown.

FIG. 2A—A Northern (upper panel) and immuno (lower panel) blot for RAN protein in R37, R37-OPN cells and cells stably transfected with an expression vector for RAN. Expression of OPN and RAN mRNA levels in lane 1 R37; lane 2; R37-RAN; lane 3 R37-OPN; lane 4 R37-OPN-RAN. βActin mRNA was assessed as control. Major hybridizing bands are shown in kilobases (kb) (upper Panel). The average fold increase for three different experiments for OPN is: lane 1=1, lane 2=1.2±0.3, lane 3=7.5±1.5 and lane 4=8±1.1 and for RAN is: lane 1=1, lane 2=6.5±0.5, lane 3=6.3±0.5 and lane 4=7.5±1.4. Cell lysates were diluted and 5 µg for RAN and β-actin and 20 µg for OPN immunoblots were loaded on a SDS 10% polyacrylamide gel, as follows: lane 1 R37; lane 2 R37-RAN; lane 3 R37-OPN; lane 4 R37-OPN-RAN. Specific proteins were detected using antibodies to OPN, RAN or β-actin. Bands were quantified using densitometric analysis and normalized against β-actin. The average fold increase for three different experiments for OPN is: lane 1=1, lane 2=1±0.2, lane 3=5.8±0.4 and lane 4=5.8±0.7 and for RAN is: lane 1=1, lane 2=4.9±0.7, lane 3=5.1±0.5 and lane 4=5.6±0.7. The results given were representative of 3 experiments.

Figure 2C:
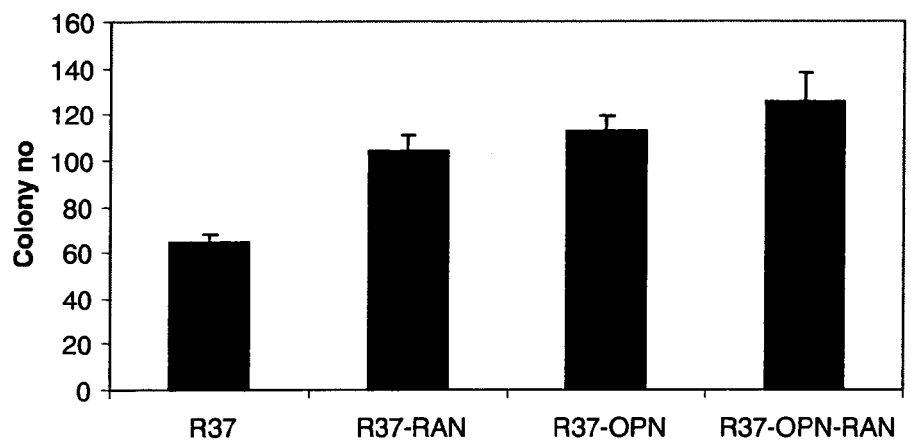

FIG. 2B—The ability of transfected cell lines to adhere to a laminin-treated surface was assessed over a 30 min period and the number of adherent cells quantified. The results were the mean±standard error from three independent experiments FIG. 2C—A soft agar assay was carried out to assess the ability of stable transfected cell lines to grow in an anchorage independent environment. The colony number was assessed after 5 days. The results were the mean standard error from three independent experiments.

Figure 2D:
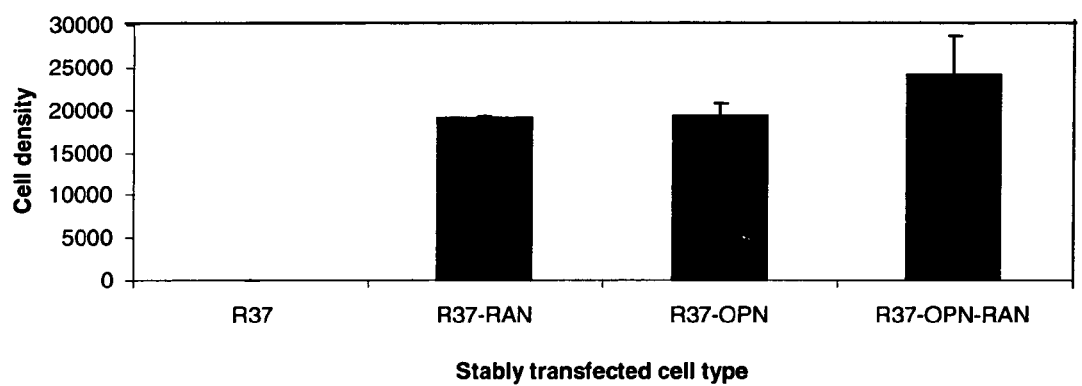

FIG. 2D—R37 and R37-OPN stably transfected with and without RAN were plated on ECM-coated filters (500 µg/ml) in Boyden chambers. The number of cells that migrated through the filter after 48 hrs was determined by staining the inserts and scanning using a digital imaging system (Experimental Procedures). The results were the mean±standard error from three independent experiments.

FIG. 3A—An immunoblot showing OPN and RAN levels in cells containing as OPN. The average fold increase for three different experiments for OPN is: lane 1=1, lane 2=4.2±0.3 and lane 3=0.8±0.15 and for RAN is: lane 1=1, lane 2=2.8±0.3 and lane 3=1±0.2.

FIG. 3B—Immunoblot showing OPN and RAN levels in cells containing siRNA-RAN. Cell lysates were diluted 20 µg (for anti-OPN) or 5 µg (for anti-RAN) loaded onto a SOS 10% polyacrylamide gel, as follows: lane 1 R37; lane 2 R37-RAN; lane 3 R37/siRNA-RAN; lane 4 R37-OPN; lane 5 R37-OPN-RAN and lane 6 R37-OPN/siRNA-RAN. Specific proteins were detected using antibodies to OPN or RAN or β-actin. Bands were quantified using densitometric analysis and quantified with respect to those of β-actin. The average fold increase for three different experiments for RAN is: lane 1=1, lane 2=3.8±0.4, lane 3=0.8±0.2, lane 4=2.6±0.2, lane 5=3±0.3 and lane 6=1±0.3 and for OPN is: lane 1=1, lane 2=1±0.3, lane 3=0.9±0.2, lane 4=4.1±0.4, lane 5=4.2 0.5 and lane 6=4.3±0.6.

Figure 3C:
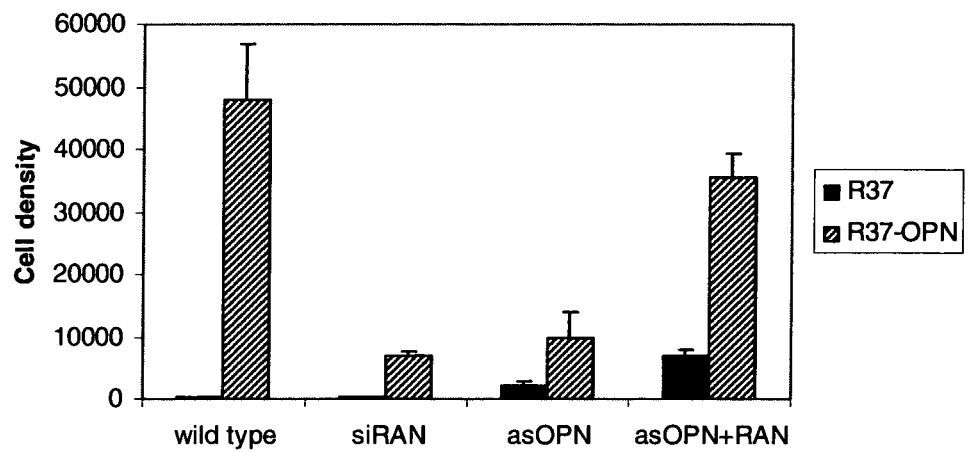

FIG. 3C—The ability of transfected cell lines to adhere to a laminin-treated surface was assessed over a 30 min period and the number of adherent cells quantified. The results were the mean±standard error of three independent experiments.

Figure 3D:
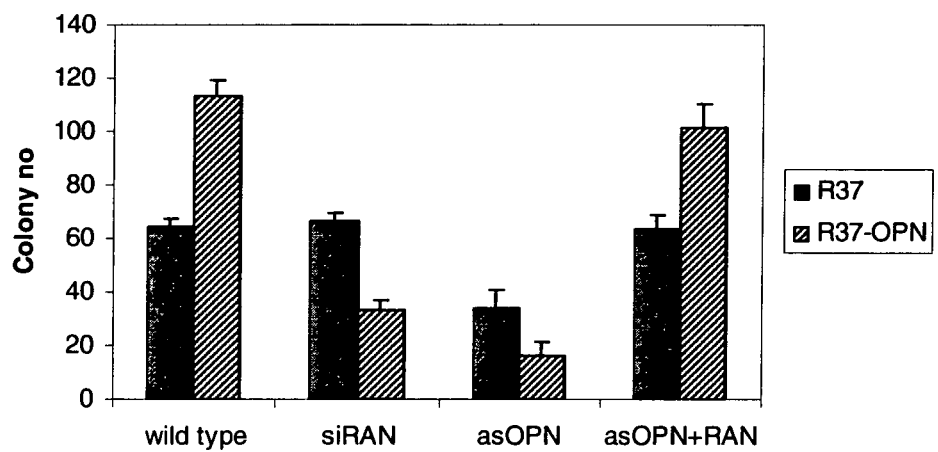

FIG. 3D—Soft agar assays were carried out to assess the ability of stable transfected cell lines to grow in an anchorage independent environment. The colony number was assessed after 5 days. The results were the mean±standard error of three independent experiments.

Figure 3E:
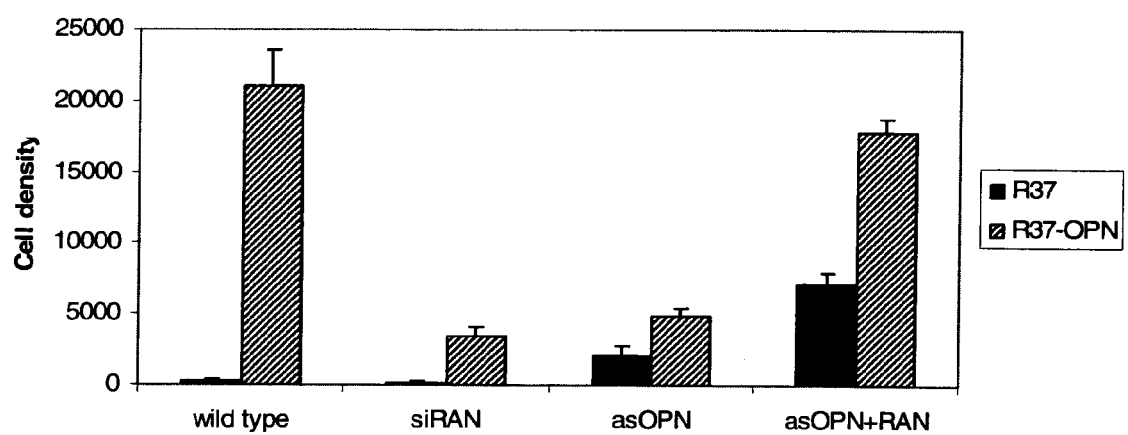

FIG. 3E—R37 and R37-OPN cells stably transfected with expression vectors for siRNA-RAN, for as-OPN or a combination for as-OPN and RAN (asOPN+RAN). Cells were plated on ECM-coated filters (500 µg/ml) in Boyden chambers. The number of cells that migrated through the filter after 48 hrs was determined by staining the inserts and scanning using a digital imaging system (Experimental Procedures). The results were the mean±standard error of three independent experiments.

FIG. 4A—Immunoblot for RAN protein with cells transfected with individual siRNA-RAN oligonucleotides. Cell lysates were diluted and 5 µg loaded onto a SDS 10% (w/w) polyacrylamide gel, as follows: lane 1 R37-OPN; lane 2 R37-OPN-oligo1; lane 3 R37-OPN-oligo2; lane 4 R37-OPN-oligo3; lane 5 R37-OPN-oligo1,2; lane 6 R37-OPN-oligo2,3; and lane 7 R37-OPN-oligo1,3. Specific proteins were detected using antibodies to RAN or β-actin. Bands were quantified using densitometric analysis and quantified with respect to those of β-actin. The results were a representative sample of three experiments.

FIG. 4B—The ability of stably transfected cell lines to adhere to a laminin treated surface was assessed over a 30 min period and the number of adherent cells quantified. All three oligonucleotides from the siRNA RAN mixture were stably transfected separately into the R37-OPN cell line.

Figure 4C:
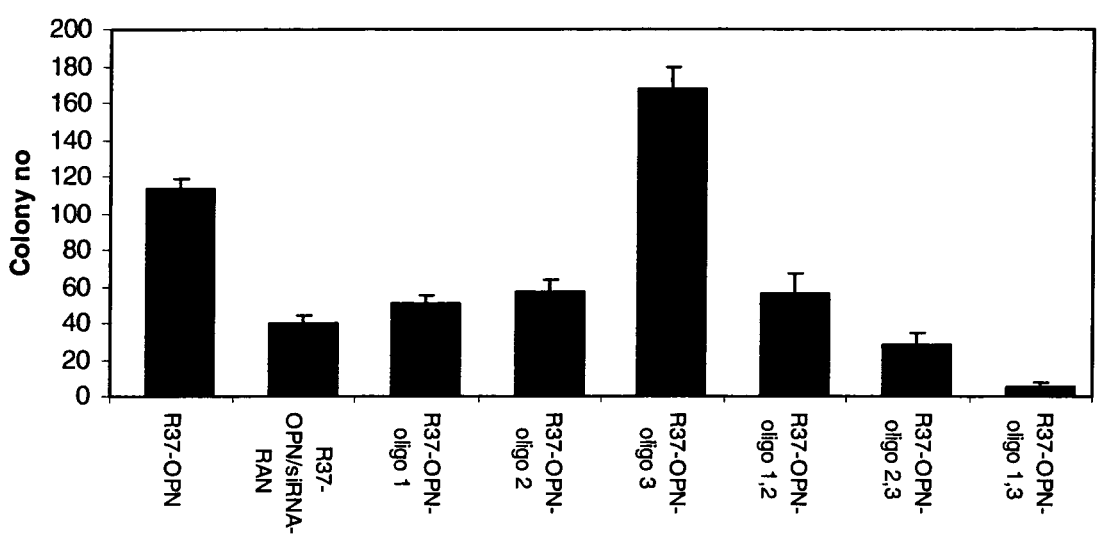

FIG. 4C—Soft agar assays were carried out to assess the ability of stable transfected cell lines to grow in an anchorage independent environment. The colony number was assessed after 5 days. The results were the mean±standard error of three independent experiments.

FIG. 5A R37 cells transfected with expression vectors, R37-Wt.RAN, R37-Wt.RAN/siRNA-RANBP1 and R37-Mut.RAN were treated with or without 50 µM of phosphoinositol 3 kinase (PI3K) inhibitor LY 294002 for 48 hr. The cells were plated on ECM-coated filters (500 µg/ml) in Boyden chambers. The number of cells that migrated through the filter after 48 hrs was determined by staining the inserts and scanning using a digital imaging system (Experimental Procedures). The results were the mean±standard error from three independent experiments.

FIG. 5B Immunodetection of Met receptor in parental R37, R37-CMV, R37-OPN and R37-RAN. 20 µg cell lysates were loaded onto a SDS 10% (W(W) polyacrylamide gel as follows: lane 1 R37, lane 2 R37-pBk-CMV; lane 3 R37-OPN; lane 4 R37-RAN. Proteins were detected in immunoblots using specific antibodies to phosphoserine 473 AkT. Bands were quantified using densitometric analysis and quantified with respect to those of β-actin. The results were a representative sample of three experiments. The average fold increase for 3 different experiments for c-MET is: lane 1=1, lane 2=1.6±0.1, lane 3=3.6±0.2, lane 4=10.4±0.8.

Figure 5C:
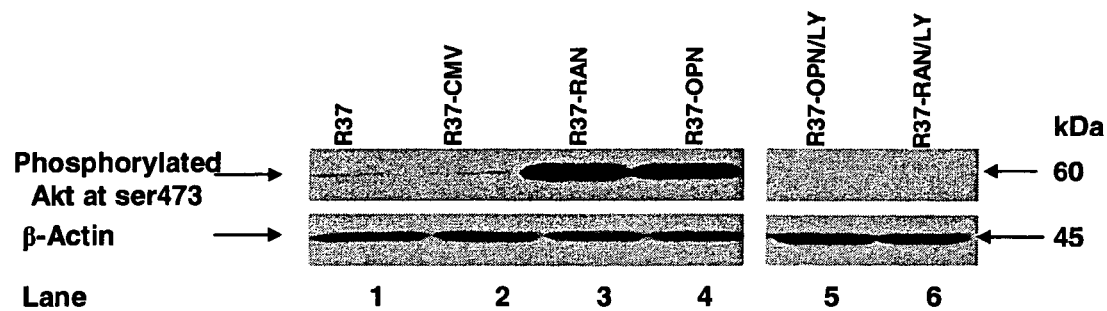

FIG. 5C Immunodetection and LY290042-inhibition of phosphorylated Akt in parental R37, R37-CMV, R37-OPN and R37-RAN cells. 20 µg cell lysates were loaded onto a SDS 10% (W(W) polyacrylamide gel as follows: lane 1 R37, lane 2 R37-pBk-CMV; lane 3 R37-RAN, lane 4 R37-OPN; lane 5 R37-OPN treated with 50 μm LY290042 for 18 hr (R37-OPN/LY); and lane 6 R37-RAN treated with 50 μm LY290042 for 18 hr (R37-RAN/LY). Proteins were detected in immunoblots using specific antibodies to phosphoserine 473 AkT. Bands were quantified using densitometric analysis and quantified with respect to those of β-actin. The results were a representative sample of three experiments. The average fold increase for 3 different experiments for phosphorylated AkT on ser473 is: lane 1=1, lane 2=2.2±0.4, lane 3=22.5±0.7, lane 4=21.1±0.5, lane 5=0±0 and lane 6=0±0.

Figure 5D:
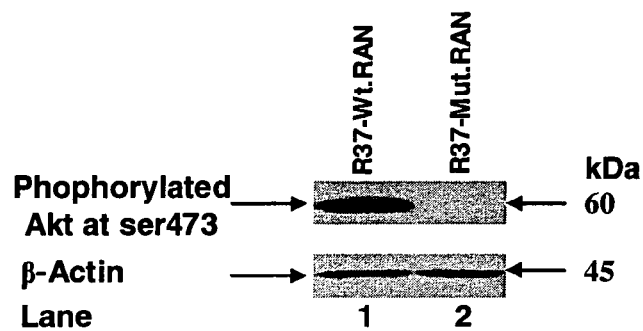

FIG. 5D Immunodetection of phosorylated AkT in Wild Type and Mutant.RAN expressing cells. 20 μg cell lysates were loaded onto a SDS 10% (W(W) polyacrylamide gel as follows: lane 1 R37-Wt.RAN; and lane 2 R37-Mut.RAN. Proteins were detected in immunoblots using specific antibodies to phosphoserine 473 AkT. Bands were quantified using densitometric analysis and quantified with respect to those of β-actin. The results were a representative sample of three experiments. The average fold increase for 3 different experiments for phosphorylated AkT on ser473 normalized to that in R37 cells (=1) is: lane 1=22.0±0.6, lane 2=0±0.

DETAILED DESCRIPTION

Markers

The expression "RAN, RAN Binding Protein 1 and derivatives thereof" includes the RAN polypeptide, an active fragment, an analog and a variant thereof together with nucleic acid sequence encoding these proteins or polypeptides and/or which hybridise to at least one of these nucleic acid sequences. It is preferred to use human RAN or its derivatives. Human RAN amino acid sequence and its coding nucleotide sequence are shown in SEQ ID No. 1 & 2 respectively.

```
                                                              SEQ ID No 1
MAAQGEPQVQFKLVLVGDGGTGKTTFVKRHLTGEFEKKYVATLGVEVH

PLVFHTNRGPIKFNVWDTAGQEKFGGLRDGYYIQAQCAIIMFDVTSRVTY

KNVPNWHRDLVRVCENIPIVLCGNKVDIKDRKVKAKSIVFHRKKNLQYYD

ISAKSNYNFEKPFLWLARKLIGDPNLEFVAMPALAPPEVVMDPALAAQYE

HDLEVAQTTALPDEDDDL
```

```
                                                              SEQ ID No 2
   1 cgcccctgct ctcgcgccgg cgtcggctgc gtctccggcg tttgaattgc gcttccgcca 61 tctttccagc ctcagtcgga cgggcgcgga ggcgcttctg gaaggaacgc cgcgatggct 121 gcgcagggag agcccccaggt ccagttcaaa cttgtattgg ttggtgatgg tggtactgga 181 aaaacgacct tcgtgaaacg tcatttgact ggtgaatttg agaagaagta tgtagccacc 241 ttgggtgttg aggttcatcc cctagtgttc cacaccaaca gaggacctat taagttcaat 301 gtatgggaca cagccggcca ggagaaattc ggtggactga gagatggcta ttatatccaa 361 gcccagtgtg ccatcataat gtttgatgta acatcgagag ttacttacaa gaatgtgcct 421 aactggcata gagatctggt acgagtgtgt gaaaacatcc ccattgtgtt gtgtggcaac 481 aaagtggata ttaaggacag gaaagtgaag gcgaaatcca ttgtcttcca ccgaaagaag 541 aatcttcagt actacgacat ttctgccaaa agtaactaca actttgaaaa gcccttcctc 601 tggcttgcta ggaagctcat tggagaccct aacttggaat tgttgccat gcctgctctc 661 gccccaccag aagttgtcat ggacccagct ttggcagcac agtatgagca cgacttagag 721 gttgctcaga caactgctct cccggatgag gatgatgacc tgtgagaatg aagctggagc 781 ccagcgtcag aagtctagtt ttataggcag ctgtcctgtg atgtcagcgg tgcagcgtgt 841 gtgccacctc attattatct agctaagcgg aacatgtgct ttatctgtgg gatgctgaag 901 gagatgagtg ggcttcggag tgaatgtggc agtttaaaaa ataacttcat tgtttggacc 961 tgcatattta gctgtttgga cgcagttgat tccttgagtt tcatatataa gactgctgca 1021 gtcacatcac aatattcagt ggtgaaatct tgtttgttac tgtcattccc attccttttc 1081 tttagaatca gaataaagtt gtatttcaaa tatctaagca agtgaactca tcccttgttt 1141 ataaatagca tttggaaacc actaaagtag ggaagtttta tgccatgtta atatttgaat 1201 tgccttgctt ttatcactta atttgaaatc tattgggtta atttctccct atgtttattt 1261 ttgtacattt gagccatgtc acacaaactg atgatgacag gtcagcagta ttctatttgg 1321 ttagaagggt tacatggtgt aaatattagt gcagttaagc taaagcagtg tttgctccac 1381 cttcatattg gctaggtagg gtcacctagg gaagcacttg ctcaaaatct gtgacctgtc
```

-continued

```
1441 agaataaaaa tgtggtttgt acatatcaaa tagatatttt aagggtaata ttttcttttta 1501 tggcaaaagt aatcatgttt taatgtagaa cctcaaacag gatggaacat cagtggatgg 1561 caggaggttg ggaattcttg ctgttaaaaa taattacaaa ttttgcactt tttgtttgaa 1621 tgttagatgc ttagtgtgaa gttgatacgc aagccg
```

Human RANBP1 amino acid sequence and its coding nucleotide sequences are shown as SEQ ID No. 3 and 4 respectively.

```
SEQ ID No. 3: Protein sequence of RANBP1
MAAAKDTHEDHDTSTENTDESNHDPQFEPIVSLPEQEIKTLEED

EEELFKMRAKLFRFASENDLPEWKERGTGDVKLLKHKEKGAIRLLMRRDKTLKI

CANHYITPMMELKPNAGSDRAWVWNTHADFADECPKPELLAIRFLNAENAQKF

KTKFEECRKEIEEREKKAGSGKNDHAEKVAEKLEALSVKEETKEDAEEKQ"

SEQ ID No. 4: Nucleotide sequence of RANBP1
   1 cgaggttcgg gtcgtggggc ggagggaaga gcgggcggc gggaggcgcc ggcgccagac 61 gcggagggaa ggagctacga gtagccgccg agaggccgcg gagccagcga cgaccgaccc 121 agccgagccg ccgccgccgc cgcgccccca tggcggccgc caaggacact catgaggacc 181 atgatacttc cactgagaat acagacgagt ccaaccatga ccctcagttt gagccaatag 241 tttctcttcc tgagcaagaa attaaaacac tggaagaaga tgaagaggaa cttttttaaaa 301 tgcgggcaaa actgttccga tttgcctctg agaacgatct cccagaatgg aaggagcgag 361 gcactggtga cgtcaagctc ctgaagcaca aggagaaagg ggccatccgc ctcctcatgc 421 ggagggacaa gaccctgaag atctgtgcca accactacat cacgccgatg atggagctga 481 agcccaacgc aggtagcgac cgtgcctggg tctggaacac ccacgctgac ttcgccgacg 541 agtgccccaa gccagagctg ctggccatcc gcttcctgaa tgctgagaat gcacagaaat 601 tcaaaacaaa gtttgaagaa tgcaggaaag agatcgaaga gagagaaaag aaagcaggat 661 caggcaaaaa tgatcatgcc gaaaaagtgg cggaaaagct agaagctctc tcggtgaagg 721 aggagaccaa ggaggatgct gaggagaagc aataaatcgt cttattttat tttcttttcc 781 tctctttcct ttccttttt taaaaaattt taccctgccc ctctttttcg gtttgttttt 841 attctttcat ttttacaagg gacgttatat aaagaactga actc
```

In embodiments, the expression "active fragment" refers to a portion of the full-length sequence which has preserved at least one of the activities or functions of the naturally occurring RAN or RANBP1. It is preferred that the active portion retains most of the biological activities of the RAN protein or RANBP1 with respect to the OPN mediated signalling pathway, its role into the transformation of a cell into a malignant cell and/or its role in metastasis.

In particular embodiments of the invention the active fragment is a fragment which presents antigenic properties. The length of such fragment comprises at least 6, up to 15, preferably 25 and more preferably 50 contiguous amino acids from SEQ ID No. 1 or SEQ ID No. 3 or derivatives thereof. An active fragment of RAN or RANBP1 can be determined using, for example, C-terminal serial deletion of RAN cDNA or RANBP1 cDNA. Said RNA cDNA deletion constructs may then be cloned into suitable plasmids, for example, but not limited to pcDNA6/His C plasmid. The activity of these deletion mutants may then be tested for biological activity as described herein. In specific embodiments, the active fragment can be derived from at least 10 consecutive amino acids of RAN, RAN Binding Protein 1 or a derivative thereof.

The expression "analog" and "variant" encompasses a RAN polypeptide sequence or RANBP1 polypeptide sequence which includes substitution of amino acids, especially a substitution(s) which is/are known for having a high probability of not leading to any significant modification of the biological activity or configuration, or folding, of the protein. These substitutions are known in the art. For example the group of arginine, lysine and histidine are known interchangeable basic amino acids. An analog or variant may comprise an amino acid sequence which is at least 70% homologous to SEQ ID NO 1, more preferably at least 80% homologous to SEQ ID NO 1, more preferably at least 90% homologous to SEQ ID NO 1, even more preferably at least 95% homologous to SEQ ID NO 1 and most preferably at least 97% homology with SEQ ID NO 1.

An analog or variant may comprise an amino acid sequence which is at least 70% homologous to SEQ ID NO 3, more preferably at least 80% homologous to SEQ ID NO 3, more preferably at least 90% homologous to SEQ ID NO 3, even more preferably at least 95% homologous to SEQ ID NO 3 and most preferably at least 97% homology with SEQ ID NO 3.

Derivatives of the RAN polypeptide or RANBP1 polypeptide also includes RAN polypeptides or RANBP1 polypeptides linked to a coupling partner, e.g. an effector molecule, a label, a drug, a toxin and/or a carrier or transport molecule. Techniques for coupling the polypeptides of the invention to both peptidyl and non-peptidyl coupling partners are well known in the art.

RAN derivatives or RANBP1 derivatives further include fusion peptides. RAN derivatives or RANBP1 polypeptide or their analogues may be fused with the constant domain of immunoglobulins (IgA, IgE, IgG, IgM), or portions thereof (CH1, CH2, CH3, or any combination thereof), resulting in chimeric polypeptides. These fusion polypeptides or proteins can facilitate purification and show an increased half-life in vivo. Such fusion proteins may be more efficient in binding and neutralizing other molecules than monomeric polypeptides or fragments thereof alone. See, e.g., Fountoulakis et al., J. Biochem., 270:3958-3964 (1995).

Fusion proteins of the invention also include RAN polypeptides or RANBP1 polypeptides fused with albumin, for example recombinant human serum albumin or fragments or variants thereof (see, e.g., U.S. Pat. No. 5,876,969, EP Patent 0413622 and U.S. Pat. No. 5,766,883).

The use of polynucleotides encoding such fusion proteins described herein are also encompassed by the invention.

Analogs for use in the present invention further include reverse- or retro-analogues of natural RAN proteins or RANBP1 protein, portions thereof or their synthetic derivatives.

RAN polypeptides or RANBP1 polypeptides may also be in the form of multimers. Thus multimers (of 2, 3 or more individual RAN polypeptide or RANBP1 polypeptide monomeric units) can be used in the method or assay according to the invention. Such multimers may be used to prepare a monomeric peptide by preparing a multimeric peptide that includes the monomeric unit, and a cleavable site (i.e., an enzymatically cleavable site), and then cleaving the multimer to yield a desired monomer.

In particular embodiments, nucleic acid sequences provided for by the expression "RAN, RAN Binding Protein 1 and derivatives thereof" comprise the nucleic acid sequences shown in SEQ ID No 2 or SEQ ID No 4, and nucleic acids which hybridise to these sequences under stringent conditions.

As used herein conditions of high stringency can be readily determined by the skilled artisan based on, for example, the length of the DNA. These conditions can be, for example, a hybridisation conducted in a solution containing 6*SSC (20*SSC represents 333 mM sodium citrate, 333 mM NaCl), 0.5% SDS and 50% formamide at 42[deg.] C., and then the hybridised products are washed in a solution of 0.1*SSC, 0.5% SDS at 68[deg.] C, or to conditions as described in Nakayama, et al., Bio-Jikken-Illustrated, vol. 2, "Idenshi-Kaiseki-No-Kiso (A Basis for Gene Analysis)", pp. 148-151, Shujunsha, 1995.

Nucleic acid sequences that can be used in the aspects of the invention comprise nucleotide sequences that are at least 70%, at least 80% identical to the naturally occurring sequences SEQ ID NO: 2 and SEQ ID NO: 4. Also contemplated are embodiments in which the nucleic acid molecules comprise a sequence at least 90%, preferably at least 95%, more preferably at least 99%, or even at least 99.8% identical to the originally occurring or native sequences SEQ ID NO: 2 and SEQ ID NO: 4. The percent identity may be determined by visual inspection and mathematical calculation or by comparing sequence information using known computer programs such as the GAP computer program.

The RAN or RANBP1 protein or polypeptides can be produced by use of the corresponding encoding polynucleotides in an expression system. In such systems the polynucleotide is inserted in an appropriate vector wherein the polynucleotide is operably linked to a control sequence which is capable of providing expression of the nucleic acid in a host cell. A variety of vectors may be used. For example suitable vectors may include viruses (eg. Vaccinia virus, adenovirus, baculovirus etc), yeast vectors, phage, chromosomes, artificial chromosomes, plasmids or cosmid DNA. In the following example of the invention the vector used is pcDNA6/His C (Invitrogen)

The vectors may be used to introduce the polynucleotide into a host cell for use in the methods of the invention. A wide variety of host cells may be used. The host cells may be prokaryotic or 'eukaryotic'. They include bacteria, eg E. Coli, yeast, insect cells and mammalian cells. Mammalian cell lines which may be used include Chinese hamster ovary cells, baby hamster kidney cells, NSO mouse melanoma cells, monkey and human cell lines and derivatives thereof and many others. The cell line which has been used in the following example as particularly suitable is Rama 37 and its subclones.

A host cell strain that modulates the expression of, modifies, and/or specifically processes the gene product may be used. Such processing may involve glycosylation, ubiquination, disulfide bond formation and general post-translational modification.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 2nd ed., Ausubel et al. eds., John Wiley & Sons, 1992 and, Molecular Cloning: a Laboratory Manual: $3^{rd}$ edition Sambrook et al., Cold Spring Harbor Laboratory Press, 2000.

In embodiments of methods of the invention, the methods may be performed using an animal model useful for screening for agents capable of modulating the effects of the RAN polypeptides or RANBP1 polypeptides. A useful genetically modified animal may comprise naturally occurring sequences of the RAN gene or RANBP1 gene or genetically altered sequences including insertions, deletions, additions, and substitutions. Preferably the animals used are transgenic animals which have germ-line insertions that are stably transmitted to all cells of progeny animals. The genetically modified animals may produce larger amounts of RAN polypeptide or RANBP1 polypeptide and would be useful disease models. Reference to larger amount includes up to about a 2, 3, and more preferably a 4 to 5 fold increase than normal.

Preferably, the genetically modified animal is a mouse, rat, guinea pig, rabbit, pig, sheep or goat. More preferably, the genetically modified animal is a mouse or rat. Most preferably, the genetically modified animal is a mouse.

The animal models of the present invention may be in the form of the animals or may be, for example, in the form of embryos for transplantation. The embryos are preferably maintained in a frozen state and may optionally be sold with instructions for use.

These animals can be obtained using recombination methods that are standard in the art. Bacteriophage P1 Cre recombinase and flp recombinase from yeast plasmids are two nonlimiting examples of site-specific DNA recombinase enzymes that leave DNA at specific target sites (box P sites for Cre recombinase and flt sites for flp recombinase).

Modulators

A modulator of the level of RAN or RAN Binding Protein 1 may be a sense or antisense polynucleotide or double stranded DNA (dsRNA), a ribozyme, a DNAzyme, methylation- or demethylation-inducing agents as well as RNAi-type agents such as siRNA.

In particular embodiments siRNA can be selected from one of SEQ ID Nos. 5, 6, 7, 8, 9 and 10.

These genetic agents can be suitably conjugated to other molecules such as small peptide or molecules that can allow an easier passage across the cell membrane or facilitate hybridisation. Said genetic agents may be used in alone or in combination with each other.

Naturally occurring protein, peptide mimetics, antibodies and non-proteinaceous chemical entities (especially small chemical molecules) are also contemplated by the present invention.

A modulator of RAN and/or RAN Binding Protein 1 can be chosen from amongst polyclonal or monoclonal antibodies raised against RAN protein or RANBP1 protein or some particular antigenic portions thereof. Monoclonal antibodies raised against human RAN polypeptides or RANBP1 polypeptides are preferred. Alternatively the antibody can be humanised or may be a chimeric antibody, fab fragment etc. Further the antibodies can advantageously be conjugated to another molecule such as a label or a cytotoxic compound.

Candidates can be chosen in the group consisting of proteins, or derivatives thereof, which are known to biologically naturally interact with the RAN protein RANBP1 protein or osteopontin.

Further, a suitable modulator may be a small molecule (usually having a molecular weight lower than 1000) which can be either obtained by computer-aided drug design or, alternatively by combinatorial chemical libraries.

Materials and Methods

Cell Lines and Cell Culture

Rat mammary (R37) nonmetastatic benign tumor-derived cell line were prepared as described previously (9) and derivative stably transformed cell subclones were cultured in Dulbecco's modified Eagle's medium (DMEM), 10% (v/v) fetal calf serum, 100 μg/ml penicillin, 100 μg/ml streptomycin (Invitrogen). The MCF-7 human breast cancer cell line was obtained from ECACC, Wiltshire (UK) and propagated in DMEM, 5% (v/v) FCS, 50 ng ml$^{-1}$ insulin, $10^{-8}$ M estradiol. The human breast cancer cell lines MDA-MB 231 and MDA-MB 435S, were obtained from ECACC, Wiltshire (UK) and were grown in RPMI supplemented with 20% (v/v) fetal calf serum, 1 mM sodium pyruvate, and 100 μg/ml penicillin-streptomycin.

Plasmids and Oligonucleotides

Expression vectors for rat OPN, OPN-pBK-CMV (Stratagene) (13) and for human RAN GTPase, RAN-pcDNA6 (Invitrogen) were prepared as described previously (13). The expression vectors for small interfering RNA to RAN and RAN binding protein 1 (RANBP1), pRETROSUPER-siRNA RAN or siRNA-RAN; and for antisense to OPN RNA, antisense-OPN-pcDNA4 or as-OPN were prepared as described below. DNA sequencing confirmed their authenticity. The specific siRNA transcripts targeted against human RAN and RANBP1 were obtained from a previously described SUPER RNAi library (Cancer Research, UK) (14). Briefly, the 19 mer sequences from the RAN gene and RANBP1 genes were converted into pairs of complementary 59 mer hairpin oligonucleotides. Three sets of complementary 59 mer oligonucleotides targeting the same gene were annealed and ligated into the pRETROSUPER vector and transfected into competent DH5α bacteria. The pRETROSUPER vector contains a phosphoglycerate kinase promoter which drives expression of the Puro resistance gene for selection in eukaryotic cells (15).

The pRETROSUPER vector is derived from the Murine Embryonic Stem Cell virus (pMSCV) and contains the pSUPER shRNA expression cassette. The hairpin oligonucleotides for the SUPER RNAi™ library are cloned downstream of the polymerase III Histone H1-RNA promoter (H1). Upon transfection into a packaging cell line, pRETROSUPER expresses a transcript containing the viral packaging signal, the H1-shRNA cassette and the puromycin resistance gene. The pRETROSUPER has a specifically designed 3'LTR that has a deletion in the LTR promoter elements. This deletion results in inactivation of the LTR mediated transcription upon retroviral integration. The phosphoglycerate kinase promoter (PGK) drives the expression of the puromycin resistance gene (puro) for selection in eukaryotic cells. The pRETROSUPER plasmid can be propagated in *E. Coli* under ampicillin (AMP) selection.

Glycerol stocks of transformants were prepared with each well containing bacteria with the 3 different short interfering RNA constructs (siRNA) targeting the same gene. DNA from all three siRNA constructs was isolated. The DNA corresponding to each siRNA construct was determined by sequencing. The siRNA oligonucleotide sequences for RAN (siRNA-RAN), designed according to the human mRNA sequence (GenBank accession numbers NM_006325, BC000852) were as follows:

```
(1) target sequence 1
(5'-AAAAACGACCTTCGTGAAACGTCAT-3') -     SEQ ID NO. 5

(2) target sequence 2
(5'-AAGCCCAGTGTGCCATCATAAT-3') -        SEQ ID NO. 6

(3) target sequence 3
(5'-AAGTATGTAGCCACCTTGGGT-3') -         SEQ ID NO. 7
(most effective-particularly when in
combination
with SEQ ID No 3)
``` and for SiRNA-RANBP1 (GenBank accession numbers NM-002882) was as follows:

```
(1) target sequence 1
(5'-TACAGACGAGTCCAACCAT-3') -     SEQ ID No 8

(2) target sequence 2
(5'-CCACTACATCACGCCGATG-3') -     SEQ ID No 9

(3) target sequence 3
(5'-GGACACTCATGAGGACCAT-3') -     SEQ ID No 10
```

Target sequence 1 showed 76% homology to rat RAN whilst target sequences 2 and 3 showed 95% homology to rat RAN. These expression vectors were termed siRNA-RAN (1), siRNA-RAN (2) and siRNA-RAN (3), respectively and similarly for SiRNA-RANBP1s.

Generation of Mutated of RAN.

The pcDNA-RAN plasmid with mutated glycine (G19) to valine (V) and glutamine (Q69) to leucine (L) (Ren et al., 1995) were generated with the QuikChange site-directed mutagenesis kit (Stratagene, La Jolla, Calif.) (El-Tanani et al., 2004). A mutant of G19V was generated by using

```
5' AAC TTG TAT TGG T TGG TGA TGt      SEQ ID NO: 11
TGG TAC TGG AAA A 3'
and 5' T TTT CCA GTA CCA aCA TCA CCA      SEQ ID NO: 12
A CCA ATA CAA GTT 3'
``` forward and reverse primers, respectively.

A mutant Q69L was generated by using

```
5' GGG ACA CAG CCG GCC tGG           SEQ ID NO: 13
AGA AAT TCG GTG GAC TGA 3'
and 5' TCA GTC CAC CGA ATT TCT           SEQ ID NO: 14
CCa GGC CGG CTG TGT CCC 3'
``` forward and reverse primers, respectively. This expression vector was termed Mut.RAN.

Production of Stable Transformant Cell Lines

R37 and derivative cell lines were cultured as outlined above. Cells were harvested and seeded in multiwell plates at $2.5 \times 10^5 / 3.5$ cm diameter well in 1 ml of serum-free medium. Initially R37 cells were transfected with expression vectors for OPN, RAN and Mut. RAN, or with both expression vectors for OPN and RAN as previously described using 1.0 mg/ml geneticin (Invitrogen) for OPN or 5 µg/ml blasticidin (Invitrogen) for RAN transfections as the selective medium (16) to generate R37-OPN, R37-RAN and R37-OPN-RAN cell lines, respectively. R37, R37-RAN, R37-Mut.RAN and R37-OPN cell lines were separately stably transfected with the siRNA plasmids containing a mixture of each individual siRNA using Lipofectamine and PLUS-C reagent (Invitrogen); these cell lines were termed R37/siRNA-RAN, R37-RAN/siRNA-RAN and R37-OPN/siRNA-RAN, respectively. R37-RAN cell lines were also transfected separately with the siRNA plasmids containing the mixture of the three individual siRNA to RANBP1; these cell lines were termed R37-RAN/siRNA-. Cells were selected using 5 µg/ml puromycin. The as-OPN construct was transfected separately into R37, R37-RAN, R37-OPN and R37-OPN-RAN cell lines, and these were stably selected using 250 µg/ml Zeocin (23); they were termed R37/as-OPN, R37-OPN/as-OPN, R37-RAN/as-OPN and R37-OPN-RAN/as-OPN cell lines. The pooled clonal cell lines were established by combining all surviving cell colonies following transfection and growth under selective pressure.

Northern Blotting

Total RNA was extracted from cells and subjected to Northern blot analysis, as previously described (21). The membranes were hybridized separately and in turn to OPN and glyceraldehyde-3-phosphate dehydrogenase (GAPD) cDNA probes and subjected to autoradiography.

Western Blotting for OPN and RAN Proteins

OPN and RAN and RANBP1 protein levels were established in the stably transfected cells by Western blotting as described previously (17). 20 µg and 5 µg of total protein respectively, from whole cell lysates of OPN transfected and RAN transfected cells were electrophoresed through 10% (w/v) polyacrylamide, 1% (w/v) SDS gels and transferred by blotting onto nitrocellulose membranes (Millipore Corporation, Watford, U.K.). The membranes were blocked by incubation with 0.02 M Tris-HCl (pH 7.0), 0.9% (w/v) NaCl, 0.1% (v/v) Tween 20 containing 5% (w/v) Marvel, for 1 hour. Monoclonal antibodies to OPN (1/500) (Developmental Studies Hybridoma Bank, Iowa City, Iowa), RAN (8 ng/ml, BD Biosciences Pharmingham, Oxford, UK) RANBP1 (Santa Cruz) and β-actin (1/5000) (Sigma) were added overnight at 4° C. Bound antibodies were located by a further incubation with 1:5000 horseradish peroxidase-conjugated rabbit antimouse Ig, visualized with Luminol Reagent (Santa Cruz Biotechnology, Inc, California, USA) and exposed to Kodak XAR5 film (Sigma, Poole, U.K.). Bands on films were quantified using a digital imaging system (Syngene, Genetool, Cambridge, England).

In Vitro Tests for Malignant/Metastatic Transformation

Cell adhesion assays were carried out as previously described (18). Briefly cells were plated at a known density ($2 \times 10^5$ cells per well) in a 6 well plate in conditioned media and allowed to adhere to laminin-coated plates for 30 min at 37° C., 5% (v/v) in an atmosphere of $CO_2$. Cells were then washed with PBS and after their removal by treatment with tryspin/EDTA, were counted and cell adhesion expressed as a percentage of those adhered compared to the total number of cells added.

Colony Formulation

Colony formation was tested in soft-agar as described previously for the bottom agar, 5 ml of 1.6% (w/v) agarose was plated in a 100-mm diameter tissue culture dish and allowed to harden. Cells were removed by trypsinization and resuspended at $1.0 \times 10^6$ cells/ml in normal medium. Nine ml of normal media (1×DMEM with 10% (v/v) FCS, 200 mM L-glutamine, 100 µg/ml penicillin, 100 µg/ml streptomycin) was added to the top of the bottom agar and 1.0 ml of cells seeded per plate. The plates were incubated at 37° C. in an atmosphere of 5% (v/v) $CO_2$ for 5-7 days and stained with 1 ml of 0.2% (w/v) crystal violet. The plates were scanned for colonies and counted using a digital imaging system (Syngene, Genetool, Cambridge, England) (19).

Invasion through Matrigel

Invasion through matrigel was measured in Boyden chamber as described previously. Biocoat 250 µg/ml Matrigel invasion chambers 6.4 mm in diameter (Falcon-Ulster Anaesthetics, Moneyrea, NI, UK) were used to assess the invasiveness of suitably transfected R37 cells, as described previously (19). Briefly, $1 \times 10^6$ cells were resuspended in 1 ml of serum-free DMEM and 100 µl added to the cell culture inserts of the upper invasion chambers on top of Biocoat 250 µg/ml matrigel coated invasion chamber. A chemoattractant, 5 µg of rat fibronectin (Gibco-BRL, U.K.) per ml in DMEM and 10% (v/v) FCS were added to the lower chambers. The cultures were incubated at 37° C. in a 5% (v/v) $CO_2$ atmosphere and allowed to invade through the matrix and the pores (8 µm) of the attached lower membrane for 48 h. The upper surfaces of the filters were wiped clean of cells and the filters were fixed by immersion in 100% (v/v) methanol and stained by Gurr's eosin and methylene blue, according to the manufacturer's instructions (BDH Laboratory Supplies, Pool, U.K). The inserts were scanned for cell density using a digital imaging system (Syngene, Genetool, Cambridge, England) (19). The PI3Kinose LY294002 inhibitor (PI3K) (2-4(4-morpholinyl)-8-phenyl-4H-1-benzopyran-4-one) was purchased from calbiochem Beeston, Nottingham, U.K. At 50 µM it is specific for PI3K without inducing apoptosis (38)

Assays for Metastasis

Pooled cells were harvested by treatment with EDTA/trypsin solutions, washed and resuspended in PBS at $10^7$ cells/ml. $2 \times 10^6$ cells in 0.2 ml were injected s.c. through the skin into the right inguinal fat pads of 6-10 week-old syngeneic female Furth-Wistar rats (Ludwig-Wistar OLA strain), 20 rats/group (12). Rats were autopsied after 12 weeks, and tumors and relevant tissues particularly the lungs and lymph nodes were examined for gross metastasis. Primary tumors and other tissues of abnormal appearance including all lungs were fixed in Methacam (methanol, Inhibisol, acetic acid: 6,3,1) embedded in paraffin-wax, sectioned and stained with haematoxylin and eosin. Five microscopic fields from two sections by two independent observers were assessed as described in Davies B R, Barraclough R, and Rudland P S. Induction of metastatic ability in a stably diploid benign rat mammary epithelial cell line by transfection with DNA from human malignant breast carcinoma cell lines. Cancer Res, 54:2785-2793., (1994) and Jamieson S, Barraclough R, and Rudland PS. Generation of metastatic variants by transfection of a nonmetastatic rat mammary epithelial cell line with DNA from a metastatic rat mammary cell line. Pathobiology, 58:329-342., (1990).

mRNA Isolation

Cells were harvested at an exponential phase for RNA isolation. Total RNA was isolated with TriZol reagent (Life Technologies, Paisley, Scotland, UK) following the manufacturer's instructions. mRNA was isolated from total RNA with a NucleoTrap mRNA extraction kit (BD Clontech, Oxford, UK) following the manufacturer's protocol.

Quantitative Real Time RT-PCR

Quantitative PCR (QPCR) was used as an independent method to probe the association of identified genes with rat benign noninvasive R37 and invasive R37-OPN cell lines and to extend the observations to human breast cancer cells (Table 1).

TABLE 1

Quantitative RT-PCR for 3 breast cancer cell lines

| Cell type | TPT1 | ARNT | ATM | RAN | OPN |
|---|---|---|---|---|---|
| MCF-7 | 1 | 1 | ND | 1 | 1 |
| MDA-MB 231 | 269 | 16.6 | 1 | 765 | 60 |
| MDA-MB 435S | 159 | 4.1 | ND | 13191 | 9785 |
| ZR-75 | — | — | — | 1 | 1 |

The differential expression of the tumor protein, translationally-controlled 1 (TPT1), aryl hydrocarbon receptor nuclear translocator (ARNT), ataxia telangiectasia mutated (ATM), and RAN GTPase (RAN) genes versus the housekeeping S18 ribosomal gene S18 was calculated for each cell line using the expression: $\Delta Ct=Ct_{target\ gene}-Ct_{S18}$. Next, MCF7 non-invasive cells:other cell ratios were calculated from the $\Delta Ct$ values as follows: $2^{-(\Delta Ct\ tumor\ cells-\Delta Ct\ MCF-7)}$. ND-not detectable.

QPCR analysis was performed using a QuantiTect SYBR® Green RT-PCR kit (Qiagen) containing a QuantiTect SYBR QuantiTect SYBR Green RT-PCR buffer, SYBR Green I dye and ROX passive reference dye. In comparing quantitative expression differentials, three different human cell lines were utilized. Each sample was run in triplicate to ensure quantitative accuracy. QPCR data are reported as a ratio of the non-invasive human breast cancer MCF-7 cells to the invasive MDA MB 231 or MDA MB 435S cells and calculated using the comparative threshold cycle (Ct) method (39). Briefly, the differential expression of different target genes versus the housekeeping gene, ribosomal RNA (S18), was first calculated for all samples using the expression: $\Delta Ct=Ct$ of the target gene-Ct of the reference (S18). MCF-7 cells were compared to the indicated cell lines using the following formula: $\Delta\Delta Ct=\Delta Ct$ value for target gene-$\Delta Ct$ value for MCF-7 cells. Values were reported as $2^{-(\Delta\Delta Ct)}$ (Ponchel et al., 2003). All reported QPCR reactions were performed and analyzed using a LightCycler rapid thermal cycler system (Roche, East Sussex, England).

Briefly, 1 µg of total RNA was reverse transcribed with Superscript II reverse transcriptase (Invitrogen, Life Technologies Ltd, Paisley, UK). The cDNA was then diluted to give 200 µg/µl prior to PCR amplification. Reactions were performed in a 10 µl volume using 200 µg of cDNA and 5 µl QuantiTect SYBR Green PCR Master Mix (Qiagen, West Sussex, UK). Control samples without reverse transcriptase enzyme were included for each cell type. The expression of TPT1, ARNT, and ATM were quantified using the following primers:

```
                                             SEQ ID NO: 15
    forward 5'-GATCGCGGACGGGTTGT-3', SEQ ID NO: 16
    reverse 5'-TTCAGCGGAGGCATTTCC-3', SEQ ID NO: 17
    forward 5'-GCTGCTGCCTACCCTAGTCTCA-3', SEQ ID NO: 18
    reverse 5'-GCTGCTCGTGTCTGGAATTGT-3'
    and SEQ ID NO: 19
    forward 5'-CAGGGTAGTTTAGTTGAGGTTGACAG-3', SEQ ID NO: 20
    reverse 5'-CTATACTGGTGGTCAGTGCCAAAGT-3'.
```

The expression of RAN was quantified using the following primers:

```
forward 5'-TACTGGAAAAACGACCTT-3',   SEQ ID NO: 21 reverse 5'-TCCCATACATTGAACTTA-3'.   SEQ ID NO: 22
```

Internal control primers of ribosomal RNA (S18) were also included and were as follows:

```
forward 5'-GTAACCCGTTGAACCCCATT-3',   SEQ ID NO: 23 reverse 5'-CCATCCAATCGGTAGTAGCG-3'.   SEQ ID NO: 24
```

The protocol included a 15 min activation step at 95° C., followed by 40 cycles of 15 sec denaturation at 94° C., 30 sec of predetermined optimum annealing temperature and extension for 30 sec at 72° C. An amplification plot of fluorescence signal versus cycle number was drawn. In the initial cycles of PCR there was little change in fluorescence signal and this defined the baseline for the amplification plot. An increase in fluorescence above the baseline indicated the detection of the accumulated PCR product. A fixed fluorescence threshold of 0.1 was set above the baseline in the exponential phase of the PCR. To confirm amplification specificity, the PCR products from each primer pair were subjected to a melting curve analysis and checked using agarose gel electrophoresis.

Rapid Amplification of cDNA Ends for Cloning of Full Length cDNA of RAN

Cloning of full length RAN cDNA was carried out by rapid amplification of cDNA ends (RACE) using a Marathon cDNA amplification Kit (Clontech) on 2 mg of poly(A)+-containing RNA derived from the MDA-MB-435S cell line. The resulting adaptor ligated ds cDNA, which represented an uncloned ds cDNA library, was used to perform 5' and 3'

RACE reactions with the following RAN gene specific primers for 5' and 3' RACE reactions respectively:

```
5'-ATGGCTGCGCAGGGAGAG-3',     SEQ ID NO: 25
5'-GGGGCGAGAGCAGGCATG-3',     SEQ ID NO: 26
``` based on the GenBank accession number NM_63258.

In Vitro Recombinant RAN and Mutant Protein Preparations

Products were generated in a coupled transcription-translation cell-free protein-synthesizing reticulocyte lysate for the expression vector of wild (Wt.) or mutant (Mut.) RAN and unprogrammed lysate for the empty vector pcDNA, as we have previously described (17,40). The proteins synthesised were confirmed by Western blotting.

GTPase Assay

The assay was performed as described in the manufacture's instructions by measuring the release of inorganic phosphate using the malachite green phosphomolybdate colaumetric assay (Innova Biosciences, UK) (41). Briefly, the assay was performed in triplicate in round bottom, 96 well polystyrene plates, which were kept on ice while preparing the reactions. Each reaction mix consisted of a complete assay buffer (0.5M Tris, HcL, pH 7.4/0.1 M MgCl2))/substrate (0.5 mM GTP). Wt. or Mut. RAN protein containing reticulocyte lysate was added to each well. Fresh Gold mix/accelerator (1/100 [v/v]) was added, followed by added stabilizer. Control samples with the complete assay buffer, but no RAN protein in unprogrammed cell lysates were also included to account for spontaneous hydrolysis of ETP. After 30 min and 60 min, the plates were analysed spectrophotometrically at a wavelength of 600 nm. A standard dilution series of known phosphate concentrations was include in the assay to quantify the extent of GTP hydrolysis from the absorptions of phosphomolybdate.

C-Met Autophosphorylation

Confluent monolayers (19-cm diameter Petri dishes) of R37, R37-pBK-CMV (R37-CMV), R37-OPN and R3-RAN cells were serum-starved overnight at 37° C., lysed in anti-phosphotyrosine RIPA Buffer (20 mM Tris-HCl, 150 mM NaCl, 2.5 mM EDTA, 10 mM NaF, 10 mM sodium pyrophosphate, 1 mM sodium vanadate, 1% Nonidet P-40, plus protease inhibitors, pH 7.5), and immunoprecipitated with anti-phosphotyrosine monoclonal antibody 4G10 bound to agarose beads (50 µl of beads/lysate; Upstate Biotechnology, Inc, USA.). Immunoprecipitated proteins were resolved by 7.5% WN SDS-PAGE and immunoblotted with mouse anti-c-Met (Santa Cruz, sc-161), as described previously (42).

AKT Phosphorylation

The R37, R37-CMV, R37-RAN and R37-OPN cells were harvested at 80% confluence from 7 cm dishes. The cell were lysed in 300 µl of 2× Loading buffer (20% glycerol (v/v), 4% SDS (w/v), 10% 2-mercaptoethanol (v/v), 126 mM Tris, pH 6.8 and coloured with bromophenol blue). The lysates were sonicated, boiled at 100° C. for 5 minutes and then centrifuged at 15000 rpm for 10 minutes. Proteins were resolved by 7.5% SDS-PAGE and immunoblofted for ser473 phosphorylated Akt.as previously (43).

Statistical Treatment of Results

All biological experiments were performed at least three times. The mean and standard error were calculated and p values less than 0.05 were considered significant as calculated using the student's t-test.

EXAMPLES

Example 1

Effect of Osteopontin Gene Expression on Cell Invasion

The inventors raised various stable cell lines from R37 cells. These were stably transfected by empty vector pBK-CMV (R37-pBK-CMV) or by the constitutively active expression vector OPN-pBK-CMV (R37-OPN cells) as described herein. Individual clones of the transformants were pooled for subsequent analysis. Immunoblot analysis using a monoclonal (MAb) antibody to OPN, which recognizes both human and rat OPN showed that the OPN protein was expressed at a low level in R37 and R37-pBK-CMV cells (FIG. 1A). In R37, R37-pBK-CMV and R37-OPN cells, the MAb to OPN recognized a protein of $M_r$ 65,000 (FIG. 1A, Lanes 1-3), consistent with the size of OPN from rat cell lines (9, 19). OPN protein expression was increased 10 fold in R37-OPN compared to R37 and R37-pBK-CMV cells (FIG. 1A). The increase in OPN protein in the R37-OPN cell line suggests that the OPN-pBK-CMV vector consistently overexpresses OPN, the empty vector pBK-CMV having no effect on OPN expression in R37 cells.

Example 2

Effect of OPN on Cellular Adhesion, Anchorage-Dependent Growth and Invasion

Adhesion of cells to laminin-coated surfaces was assayed using a dye based system. R37-OPN cells showed a 9.2 and 8 fold increase in cell adhesion to laminin-coated dishes, in comparison with R37 and R37-pBK-CMV cells, respectively (p<0.01) (FIG. 1B). Colony formation was assayed in soft agar, R37-OPN cells induced a 1.8 and 2.3 fold increase in colony number per plate compared to R37 and R37-pBK-CMV cells, respectively (p<0.01) (FIG. 1C). The ability of cells to migrate through a reconstituted three dimensional collagen gel (Matrigel) and appear on the underside of a polycarbonate membrane was tested as an assay for cell invasion. The number of cells on the underside of the membrane were stained, scanned and counted using a digital imaging system in Experimental procedures (19). Migration of R37-OPN transformants was 913 and 1006 fold greater than the parental R37 and R37-pBK-CMV cells, respectively (p=0.002) (FIG. 1D). These results suggest that high levels of OPN induce cell adhesion, anchorage independent growth and invasion in vitro.

Example 3

Quantitative Real Time PCR and Expression of RAN

Four of the highest differentially expressed genes that were also associated with invasion and/or malignancy were chosen from the total number of 1686 (data not shown) for validation by quantitative real-time PCR analysis (OPCR) (Table 1) using the relatively non-invasive MCF-7 and the highly invasive MDA-MB-231 and MDA-MB-435S human breast cancer cell lines (Nam et al., 2004). The four genes encode for tumor protein translationally-controlled (TPTI), aryl hydrocarbon receptor nuclear translocator (ARNT), ataxia telangiectasia mutated (ATM) and RAN GTPase (RAN). MCF-7 cell: other cell ratios were calculated using the comparative threshold cycle (Ct) method (29) after normalization to a control housekeeping gene for ribosomal RNA S18. The highly invasive malignant cell lines MDA-MB-231 and MDA-MB-435S showed a 269 and 159 fold increase in TPTI expression, respectively, in comparison with the relatively non-invasive malignant cell line MCF-7. MDA-MB-231 and MDA-MB-435S cells showed a 16.6 and 4.1 fold increase in ARNT expression, respectively, in comparison with MCF-7 cells. ATM was undetectable in both MCF-7 and MDA-MB-435S, but a small amount was detected in MDA-MB-231 cells (Table 1). However, the most differentially expressed gene of the four was RAN GTPase. Thus the invasive cell lines MDA-MD-435s and MDA-MB-231 showed a 13191 and 765 fold increase, respectively, in RAN expression compared to MCF-7 cells and they also showed a 9785 and 60 fold increase in levels of OPN (Table 1). The relatively non-invasive breast cancer cell line ZR-75 showed almost identical levels of low expression of RAN and OPN to those of the MCF-7 cell line (Table 1).

Example 4

Effect of RAN on Benign R37 Cells and Invasive R37-OPN Cells

Stable transfection of R37 cells with an expression vector for RAN increased RAN and RAN protein expression by 6 fold and 5 fold respectively, but did not affect OPN levels using Northern and Western blot analysis. Moreover, stable transfection of R37-OPN cells with an expression vector for RAN barely affected RAN or OPN levels of mRNA and protein (FIG. 2A). In contrast, transfection of R37 cells with the expression vector for OPN increased the mRNA and protein for RAN by similar 6 and 5 folds, respectively. All results were normalized using a housekeeping gene, beta-actin and quantified using densitometry readings. Adhesion of the transfected RAN cells to laminin-coated surfaces was assayed by a dye-based system. Transfection of RAN into R37 cells, designated R37-RAN, produced a 3.1 fold increase ($p<0.01$) in adhesion to laminin-coated dishes whilst transfection of expression vector for OPN, designated R37-OPN, produced an 11-fold increase ($P<0.01$). In contrast RAN produced no further increase in adhesion of R37-OPN cells (FIG. 2B). Colony formation was assayed in soft agar to test anchorage-independent growth. Stable transfection of the RAN expression vector into R37 and R37-OPN cells, designated R37-RAN, R37-OPN-RAN, induced a significant 1.6 fold ($p<0.01$) and a nonsignificant 1.1 fold ($p>0.05$) increase in colony number per plate compared to the respective R37 and R37-OPN controls (FIG. 2C). The ability of cells to invade through Matrigel was tested as an assay for cell invasion. The migration of R37RAN transfectants was increased by 907 fold ($p<0.01$) over the parental R37 cells, approaching that of R37-OPN cells, but RAN overexpression had no significant effect on cell migration in R37-OPN cells ($p=0.5$) (FIG. 2D).

Example 5

Effect of OPN Antisense cDNA (as-OPN) and siRNA-RAN on Osteopontin and RAN Protein Expression Immunoblot analysis using MAb to OPN and RAN which recognize both human and rat OPN and RAN demonstrated that the OPN and RAN proteins were both reduced in R37-OPN/as-OPN cells compared to the control cells, R37-OPN, (FIG. 3A) by factors of 5 and 3 fold respectively. In contrast, only RAN protein levels were significantly reduced in the R37-OPN/siRNA-RAN cells compared to the R37-OPN cells by a factor of 13 fold, there was no significant reduction in OPN protein (FIG. 3B). Western blots were performed from a pool of cloned-cell extracts and the MAb to OPN and RAN recognized proteins of Mr 65,000 and 25,000 Da, respectively (FIGS. 3A and B), consistent with the size of OPN (5,16) and RAN from rat cell lines (22). These results suggest that inhibiting OPN expression inhibits that of RAN, but inhibiting RAN expression does not inhibit that of OPN. In R37-RAN cells in which the binding protein for RAN, RANBP1 was inhibited by transfection with siRNA-RANBP1, the level of RAN protein itself was relatively unaffected (1.0 fold reduction), whereas that of the RANBP1 was reduced by a factor 8 in the R37-RAN/siRNA-RANBP1 cells (data not shown).

Example 6

Effect of Inhibiting RAN and OPN Expression on Cellular Properties

Transfection of R37-OPN, cells with expression vectors for siRNA-RAN and as-OPN significantly reduced cell adhesion by 8 and 5.3 fold, respectively ($p<0.01$) to levels close to that of R37 cells alone. There was little or no effect of these transfections on R37 cells alone (FIG. 3C). When the expression vector for RAN was stably co-transfected into R37/as-OPN cells, designated R37-RAN/as-OPN, cell adhesion increased 3.7 fold compared to R37/as-OPN cells ($p=0.0004$). When the expression vector for RAN was co-transfected with that for as-OPN in R37-OPN cells, designated R37-OPN-RAN/as-OPN, cell adhesion significantly increased by 3.6 fold when compared to R37-OPN/as-OPN cells ($p<0.01$), overcoming the inhibitory effect of expression of as-OPN (FIG. 3C). Stable transfection of R37-OPN cells separately with expression vectors for siRNA-RAN and as-OPN significantly reduced colony formation in soft agar by 3.4 and 6.9 fold, respectively ($p<0.01$). There was little effect of siRNA-RAN expression on R37 colony cell growth but a significant 2 fold reduction in R37/as-OPN cells ($p=0.02$) (FIG. 3D). When RAN was stably co-transfected into R37/as-OPN cells, designated R37-RAN/as-OPN, colony formation was increased 1.9 fold compared to R37/as-OPN cells ($p=0.02$), rising almost to that of the original R37 cells. Reintroduction of the RAN expression vector into R37-OPN/as-OPN known as R37-OPN-RAN/as-OPN cells caused colony formation to increase by 6 fold over that of the R37-OPN/as-OPN cells ($p<0.01$), similar to the original level in R37-OPN cells. Stable transfection of R37 with expression vector for siRNA or as-OPN had little or no effect on invasion in R37 cells. Stable transfection of R37-OPN cells with expression vectors for siRNA-RAN or as-OPN reduced invasion of R37-OPN cells by 4.4 and 2.5 fold, respectively (FIG. 3E). Furthermore, stable transfection of R37RAN cells with an expression vector for SiRNA-RANBP1 reduced invasion of R37 cells by 70%. When the expression vector for RAN was stably co-transfected into R37/as-OPN cells, designated R37-RAN/as-OPN, invasion increased 3.2 fold compared to R37/as-OPN cells ($p=0.04$). In contrast, transfection of R37 with expression vector for Mut.RAN had little effect on invasion in R37 cells compared to WT.RAN (FIG. 5A). When RAN was overexpressed with as-OPN in R37-OPN cells, designated R37-OPN-RAN/as-OPN, cell invasion significantly increased by 1.5 fold when compared to R37-OPN/as-OPN cells, overcoming the inhibitory effect of as-OPN (FIG. 3E).

Example 7

Effect of Permanent Transfection of RAN on Metastasis In Vivo

Transfection of Rama 37 cells with RAN construct, RAN-as-OPN construct, OPN pBKCMV/siRNA RAN or pBKCMV vector alone yielded 1- to 5-mm diameter colonies of cells that were visible after 10 days. Colonies of R37-OPN, R37-OPN/siRNA RAN, R37-RAN, R37-RAN/as-OPN transfectants were first picked, and then the remaining colonies were pooled. The pooled and individual cell colonies continued to grow in selective medium for up to 12 passages, whereas all of the parental untransfected Rama 37 cells died within 4 days in this medium. Injection of each pool of the above transfectants into 20 female rats induced tumors in 14/17 (64%), 0/20 (0%), 10/20 (50%), and 10/19 (53%) animals, respectively of the tumor-bearing animals (Fisher exact test AvB, P=0.00003; AvC, P=1; AvD, P=0.0005; AvE, P=0.0004; BvC, P=0.00001; DvE, P=1; Table 2).

TABLE 2

Comparison of the incidence of metastasis produced by permanently transfected cell lines.

| Transformants | Tumor incidence[a] (100%) | Incidence of Metastasis[b] (100%) |
|---|---|---|
| R37-pBK-CMV | 18/20 (90%) | 0/18 (0%) |
| R37-OPN | 17/20 (85%) | 11/17[c] (65%) |
| R37-OPN/siRNA-RAN | 20/20 (100%) | 0/20 (0%) |
| R37-RAN | 20/20 (100%) | 10/20[c] (50%) |
| R37-RAN/as-OPN | 19/20 (95%) | 10/19[c] (53%) |

[a] Number of tumors/number of animals injected.
[b] Number of animals with metastases/number of animals with primary tumors.
[c] R37-OPN, R37-RAN, R37-RAN/as-OPN were highly significantly different from R37-pBK-CMV, R37-OPN/siRNA-RAN (Fisher's Exact test), (p ≤ 0.00003), whereas there was no significant difference between R37-pBK-CMV and R37-OPN/siRNA-RAN (p = 1) and between R37-OPN and R37-RAN and R37-RAN/as-OPN (p ≥ 0.51).

The majority of the metastases occurred in the lungs, with a few metastases in the lymph nodes, but no metastatic deposits were observed in other organs. The histological appearance of primary tumors from all of the four groups were similar, primarily consisting of spindle cells admixed with more cuboidal, epithelial-like cells.

Example 8

Establishing the Active Oligonucleotide Sequence in RAN siRNA Mixture

The siRNA-RAN consisted of a mixture of three different oligonucleotide sequences. When each of the three oligos were analyzed by Western blot for RAN protein expression they showed 1.6, 2.6 and 9.6 fold reduction in RAN protein expression compared to R37-OPN cells for oligos 1 (SEQ ID NO: 5), 2 (SEQ ID NO: 6) and 3 (SEQ ID NO: 7) respectively, with oligo 3 having the greatest effect (FIG. 4A, lanes 2-4). Combinations of oligos 1, 2, oligos 2, 3 and oligos 1, 3 showed 33.4, 9.5 and 21.8 fold reduction in protein expression, respectively (FIG. 4A, lanes 5-7). Each oligonucleotide was tested separately to assess it effect on cell adhesion. R37-OPN cells were stably transfected with each one separately or in combination, designated R37-OPN-oligo 1; R37-OPN-oligo 2; R37-OPN-oligo 3; R37-OPN-oligo 1; 2, R37-OPN-oligo 2, 3; R37-OPN-oligo 1, 3. R37-OPN-oligo 1 decreased cell adhesion 1.5 fold, R37-OPN-oligo 2 by 1.4 fold and R37-OPN-oligo 3 by 2.5 fold. All three oligo's were able to decrease cell adhesion significantly with oligo 3 having the greatest effect (p=0.01, p=0.02 and p<0.005, respectively). R37-OPN-oligo 1, 2, R37-OPN-oligo 2, 3 and R37-OPN-oligo 1, 3 cells showed a significant decrease in cell adhesion by 2.6, 2.1 and 14.3 fold respectively, compared to R37-OPN cells (p=0.002, p=0.001 and p<0.005, respectively). The combination of oligo1, 3 showed a reduction in adhesion to the same level as transfection with the combined siRNA-RAN construct (p<0.005) (FIG. 4B).

Each oligonucleotide was also tested separately and in combination for its ability to cause a decrease in colony formation in R37-OPN cells. R37-OPN-oligo 1 and R37-OPN-oligo 2 cells caused a significant decrease in colony formation (2.3 and 2.0 fold decrease, p<0.005, respectively). All combinations of oligonucleotides caused a significant reduction in colony formation. R37-OPN-oligo1, 2 cells showed a 2.0 fold reduction, R37-OPN-oligo 2, 3 a 4.0 fold reduction which R37-OPN-oligo1, 3 cells showed the greatest reduction in colony formation by 23 fold (p<0.005) (FIG. 4C). These results suggest that the capacity of the above oligonucleotides to inhibit RAN mediated cell adhesion and colony formation is related to their capacity to inhibit RAN expression.

Example 9

Mechanistic Effect of RAN on Invasion In Vitro

To test whether the invasive phenotype induced by RAN was mediated through its specific binding proteins and/or through its GTPase activity (41,44), both activities were inhibited separately in R37-RAN cells. In R37-RAN cells in which the binding protein for RAN RANBP1 was inhibited by transfection with siRNA-RANBP1, the level of RAN protein itself was relatively unaffected (1.0+S.D. level compared to untransfeced R37-RAN), whereas that of the RANBP1 was reduced by 8+S.D.-fold in the R37-RAN/siRNA-RANBP1 cells (data not shown). A double mutant in the GTP binding pocket of RAN was also constructed, Mut.RAN (Materials and Methods) which, when expressed in a reticulocyte cell-free protein-synthesising system produced a lower 6-8 fold rate of GTP hydrolysis over the wild type (Wt.) RAN, its activity being barely detectable above that in unprogrammed cell lysates (Table 3).

TABLE 3

Phosphate released by lysates containing Wt. and Mut.RAN GTPase

| | 30 min. | 60 min. |
|---|---|---|
| Unprogrammed | 1 | 1 |
| WT.RAN | 20 ± 2 | 30 ± 3.5 |
| Mut.RAN | 2.5 ± 0.5 | 5 ± 1.5 |

Reaction kinetics for Wt. and Mut.RAN were assayed by measuring the inorganic phosphate released upon GTP hydrolysis. The inorganic phosphate ($P_i$) values were obtained from standard curves and are averages of three independent determinations.

The R37-RAN/siRNA-RANBP1 and the R37-Mut.RAN cells produced reductions of 68% and 82%, respectively, in the level of invasion, in comparison with the R37-RAN cells (FIG. 5A). To test whether RAN/RANBP1 signaled increased invasion through the c-Met receptor and activation of Akt (44), levels of phosphorylation of both these proteins were measured in R37-RAN and R37-OPN cells using either a combination of antiphosphotyrosine, anti-c-Met antibodies or a specific antibody to phosphoserine 473 of Akt (Materials and Methods). Both phosphoproteins of 145 kDa and 65 kDa corresponding to c-Met B-subunit and Akt were present at much higher levels in the R37-OPN (c-Met 3.6±0.2 fold, Akt 21.1±0.5 fold) and R37-RAN (c-Met 10.4±0.8 fold, Akt 22.5±0.7 fold) cells than in the untransfected Rama 37 cells (c-Met=1 fold, Akt=1 fold) or vector alone transfected Rama 37 cells (c-Met 1.6±0.1 Fold, Akt 2.2±0.4 fold) when normalized to total protein and to Bactin, respectively (FIG. 5B, C). R37-Mut.RAN cells contained a undetectable level of phosphorylated Akt, similar to that in parental Rama 37 cells (=1 fold) (FIG. 5D). Inhibition of PI3 kinase (P13K) by exposure of the R37-RAN and R37-OPN cells to 50 μM LY294002 (38) completely abolished detectable levels of phosphorylated Akt (FIG. 5C) and reduced invasion of R37-RAN cells by 71% to a level similar to that seen in the R37-Wt.RAN/siRNA-RANBP1 cells (FIG. 5A).

Example 10

Effect of RAN Mutation on GTPase Activity

Reticuloyte protein-synthesising lysates were primed with expression vectors for Wt. RAN and a double mutant in the GTP binding pocket, Mut. RAN. The Wt. and Mut. RAN GTPase activity was determined by using the malachite green-phosphomolybdate calorimetric assay (Innova Biosciences, UK) (41) that measures inorganic phosphate released upon GTP hydrolysis. GTP hydrolysis was measured for 30 and 60 min periods. The double Mut. RAN was 6-8 times less than that of the Wt.RAN (Table 3).

Benign R37 rat mammary cell line stably transfected with an expression vector for OPN, termed R37-OPN cells increased OPN expression by 10 fold in excess of that in parental R37 cells. Increased expression of this magnitude is sufficient to induce the invasive phenotype in vitro (1), enhance cellular migration through Matrigel (24) and induce metastasis in syngeneic rats in vivo in this R37 system (4). In the present study, OPN cDNA overexpression in R37-OPN cells is associated with enhanced cellular adhesion to laminin-coated surfaces, enhanced anchorage-independent growth in soft agar and enhanced cellular invasion through Matrigel. R37 cells thus provide a robust system for the study of OPN-induced changes in the parental R37 cells that leads to the invasive phenotype in vitro and, by analogy, to the metastatic state in vivo (4). The inventors have identified the G protein RAN as a potential downstream effector of the OPN-induced signalling network that can lead to invasion and ultimately metastasis. Further, the inventors have identified differentially expressed genes whose proteins can interact with and possess some function of RAN, these include p27 and RAG-1, MDM 2, RAN binding protein 5, adenovirus EIA oncoprotein, RAN promoter activated protein SpI, HLA-A, and androgen receptor associated protein 24.

When siRNA-RAN was transfected into the R37-OPN cells, it was determined to inhibit the production of OPN, whilst transfection of the expression vector for as-OPN into RAN expressing R37 cells failed to inhibit the expression of RAN. Moreover, when an expression vector for RAN was transfected into R37 cells independently of OPN, it also had the ability to transform their phenotype in the same manner as that of the expression vector for OPN by inducing increased cell adhesion to laminin-coated surfaces, increased anchorage-independent cell growth and increased cell invasion through Matrigel, properties identified with the malignant state in vitro and associated with increased metastasis in vivo. Permanent transfection of Rama 37 and R37-as-OPN cells with the RAN cDNA in its expression vector causes elevated level of RAN proteins and confers the ability to metastatsize in syngeneic rats. Since the relatively non-invasive MCF-7 and ZR-75 express low levels of both OPN and RAN and both levels are increased in the invasive breast cancer cell lines MDA MB 435S and MDA MB 231, this suggests that their levels are coordinately regulated.

The inventors have determined that stable transfection of non-invasive R37 cells with an expression vector for RAN induces the invasive/metastatic phenotype in culture characterized by increased cell adhesion, anchorage independent growth and invasion through Matrigel and in vivo by metastasis in syngeneic rats. Conversely, stable transfection of invasive R37-OPN cells with RAN siRNA down-regulates RAN expression and inhibits the invasive/metastatic phenotype. Further, stable transfection of R37 cells with Mut.RAN significantly inhibits invasion.

The inventors results show that RAN can trigger the cells to metastatsize in vivo independently of OPN and it is the key OPN intermediate molecule. Thus expression of RAN alone is able to convert R37 cells to a malignant, metastatic phenotype in vitro and in vivo. The fact that expression of three siRNA oligonucleotides targeted against RAN inhibits the three properties associated with the malignant, metastatic state in R37-OPN cells, and that overexpression of RAN in OPN-silenced R37-OPN cells recreates the malignant, metastatic state are consistent with RAN being a downstream effector of the same malignant, metastatic state induced by OPN. This conclusion is confirmed by the similar incremental decreases in expression of RAN protein (FIG. 4A) and in cell adhesion (FIG. 4B) and anchorage-independent growth (FIG. 4C) when the R37-OPN cells are transfected singly or in binary combinations with the three siRNA oligonucleotides targeted against RAN. Moreover, the expression of RAN in OPN-silenced R37-OPN cells fully restore their invasive potential in vitro and in vivo, respectively (FIG. 3E, table 2) suggests that RAN alone and also play an important role in OPN's induction of invasion in the R37 cell system.

In addition, it has been determined that overexpression of RAN in R37 cells increased both MET receptor and Akt phosphorylation and treatment of R37-RAN cells with a phosphoinositol 3 kinase (P13K) inhibitor LY 294002, completely abolished Akt phosphorylation and reduced cell invasion.

The inventors have further determined that an inhibitor of RAN mediated invasion by R37 cells is phosphoinositol 3 kinase (P13K) inhibitor LY 294002. The inventors have also determined that treatment of R37-RAN cells with LY 294002 inhibits Akt phosphorlyation.

Various modifications may be made to the invention herein described without departing from the scope thereof.

References

1. Behrend, E. I., Craig, A. M., Wilson, S. M., Denhardt, D. T., and Chambers, A. F. Reduced malignancy of ras-transformed NIH 3T3 cells expressing antisense osteopontin RNA. Cancer Res, 54:832-837., 1994.
2. Euer, N., Schwirzke, M., Evtimova, V., Burtscher, H., Jarsch, M., Tarin, D., and Weidle, U. H. Identification of genes associated with metastasis of mammary carcinoma in metastatic versus non-metastatic cell lines. Anticancer Res, 22: 733-740., 2002.
3. Tuck, A. B., Hota, C., and Chambers, A. F. Osteopontin (OPN)-induced increase in human mammary epithelial cell invasiveness is urokinase (uPA)-dependent. Breast Cancer Res Treat, 70:197-204., 2001.
4. Oates, A. J., Barraclough, R., and Rudland, P. S. The identification of osteopontin as a metastasis-related gene product in a rodent mammary tumour model. Oncogene, 13:97-104., 1996.
5. Rudland, P. S., Platt-Higgins, A., Renshaw, C., West, C. R., Winstanley, J. H., Robertson, L., and Barraclough, R. Prognostic significance of the metastasis-inducing protein S100A4 (p9Ka) in human breast cancer. Cancer Res, 60:1595-1603., 2000.
6. Tuck, A. B., O'Malley, F. P., Singhal, H., Harris, J. F., Tonkin, K. S., Kerkviiet, N., Saad, Z., Doig, G. S., and Chambers, A. F. Osteopontin expression in a group of lymph node negative breast cancer patients. Int J Cancer, 79: 502-508., 1998.
7. Rudland, P. S., Platt-Higgins, A., El-Tanani, M., De Silva Rudland, S., Barraclough, R., Winstanley, J. H., Howitt, R., and West, C. R. Prognostic significance of the metastasis-associated protein osteopontin in human breast cancer. Cancer Res, 62: 3417-3427., 2002.
8. Singhal, H., Bautista, D. S., Tonkin, K. S., O'Malley, F. P., Tuck, A. B., Chambers, A. F., and Harris, J. F. Elevated plasma osteopontin in metastatic breast cancer associated with increased tumor burden and decreased survival. Clin Cancer Res, 3: 605-611., 1997.

9. Dunnington, D. J., Hughes, C. M., Monaghan, P., and Rudiand, P. S. Phenotypic instability of rat mammary tumor epithelial cells. J Natl Cancer Inst, 71: 1227-1240., 1983.

13. Liu, D., Rudland, P. S., Sibson, D. R., and Barraclough, R. Identification of mRNAs differentially-expressed between benign and malignant breast tumour cells. Br J Cancer, 87: 423-431., 2002.

14. Berns, K., Hijmans, E. M., Mullenders, J., Brummelkamp, T. R., Velds, A., Heimerikx, M., Kerkhoven, R. M., Madiredjo, M., Nijkamp, W., Weigelt, B., Agami, R., Ge, W., Cavet, G., Linsley, P. S., Beijersbergen, R. L., and Bernards, R. A large-scale RNAi screen in human cells identifies new components of the p53 pathway. Nature, 428:431-437., 2004.

15. Brummelkamp, T. R., Bernards, R., and Agami, R. Stable suppression of tumorigenicity by virus-mediated RNA interference. Cancer Cell, 2: 243-247, 2002.

16. El-Tanani, M., Barraclough, R., Wilkinson, M. C., and Rudland, P. S. Metastasis-inducing DNA regulates the expression of the osteopontin gene by binding the transcription factor Tcf-4. Cancer Res, 61: 5619-5629., 2001.

17. El-Tanani, M., Platt-Higgins, A., Rudland, P. S., and Campbell, F. C. Ets gene, PEA3 cooperates with beta-Catenin-Lef-1 and c-jun in regulation of Osteopontin transcription. J Biol Chem, 5:5, 2004.

18. Mayo, M. W. and Baldwin, A. S. The transcription factor NF-kappaB: control of oncogenesis and cancer therapy resistance. Biochim Biophys Acta, 1470: M55-62, 2000.

19. Fenrick, R., Wang, L., Nip, J., Amann, J. M., Rooney, R. J., Walker-Daniels, J., Crawford, H. C., Hulboy, D. L., Kinch, M. S., Matrisian, L. M., and Hiebert, S. W. TEL, a putative tumor suppressor, modulates cell growth and cell morphology of ras-transformed cells while repressing the transcription of stromelysin-1. Mol Cell Biol, 20: 5828-5839., 2000.

20. Davies, B. R., Barraclough, R., and Rudland, P. S. Induction of metastatic ability in a stably diploid benign rat mammary epithelial cell line by transfection with DNA from human malignant breast carcinoma cell lines. Cancer Res, 54:2785-2793., 1994.

21. Jamieson, S., Barraclough, R., and Rudland, P. S. Generation of metastatic variants by transfection of a nonmetastatic rat mammary epithelial cell line with DNA from a metastatic rat mammary cell line. Pathobiology, 58:329-342., 1990.

23. Chen, H., Ke, Y., Oates, A. J., Barraclough, R., and Rudland, P. S. Isolation of and effector for metastasis-inducing DNAs from a human metastatic carcinoma cell line. Oncogene, 14:1581-1588., 1997.

24. Su, L., Mukherjee, A. B., and Mukherjee, B. B. Expression of antisense osteopontin RNA inhibits tumor promoter-induced neoplastic transformation of mouse JB6 epidermal cells. Oncogene, 10: 2163-2169., 1995.

26. Lounsbury, K. M., Richards, S. A., Carey, K. L., and Macara, I. G. Mutations within the Ran/TC4 GTPase. Effects on regulatory factor interactions and subcellular localization. J Biol Chem, 271:32834-32841., 1996.

27. Pihan, G. A. and Doxsey, S. J. The mitotic machinery as a source of genetic instability in cancer. Semin Cancer Biol, 9: 289-302., 1999.

28. Azuma, K., Sasada, T., Takedatsu, H., Shomura, H., Koga, M., Maeda, Y., Yao, A., Hirai, T., Takabayashi, A., Shichijo, S., and Itoh, K. Ran, a small GTPase gene, encodes cytotoxic T lymphocyte (CTL) epitopes capable of inducing HLA-A33-restricted and tumor-reactive CTLs in cancer patients. Clin Cancer Res, 10: 6695-6702., 2004.

29. Hao, X., Sun, B., Hu, L., Lahdesmaki, H., Dunmire, V., Feng, Y., Zhang, S. W., Wang, H., Wu, C., Fuller, G. N., Symmans, W. F., Shmulevich, I., and Zhang, W. Differential gene and protein expression in primary breast malignancies and their lymph node metastases as revealed by combined cDNA microarray and tissue microarray analysis. Cancer, 100: 1110-1122., 2004.

30. De Luca, A., Mangiacasale, R., Severino, A., Malquori, L., Baldi, A., Palena, A., Mileo, A. M., Lavia, P., and Paggi, M. G. E1A deregulates the centrosome cycle in a Ran GTPase-dependent manner. Cancer Res, 63: 1430-1437., 2003.

31. Frisch, S. M. and Mymryk, J. S. Adenovirus-5 E1A: paradox and paradigm. Nat Rev Mol Cell Biol, 3: 441-452., 2002.

32. Teodoro, J. G., Shore, G. C., and Branton, P. E. Adenovirus E1A proteins induce apoptosis by both p53-dependent and p53-independent mechanisms. Oncogene, 11: 467-474., 1995.

33. Moye, V. E., Barraclough, R., West, C., Rudland, P. S., Jenkinson, S. R., and West, C. R. Osteopontin expression correlates with adhesive and metastatic potential in metastasis-inducing DNA-transfected rat mammary cell lines.

34. Aplin, A. E. and Juliano, R. L. Regulation of nucleocytoplasmic trafficking by cell adhesion receptors and the cytoskeleton. J Cell Biol, 155:187-191. Epub 2001 October 2015., 2001.

35. Bamba, C., Bobinnec, Y., Fukuda, M., and Nishida, E. The GTPase Ran regulates chromosome positioning and nuclear envelope assembly in vivo. Curr Biol, 12: 503-507., 2002.

36. Moore, J. D. The Ran-GTPase and cell-cycle control. Bioessays, 23: 77-85., 2001.

37. Denti, S., Sirri, A., Cheli, A., Rogge, L., Innamorati, G., Putignano, S., Fabbri, M., Pardi, R., and Bianchi, E. Ran-BPM is a phosphoprotein that associates with the plasma membrane and interacts with the integrin LFA-1. J Biol Chem, 279:13027-13034, 2004.

38. Davies, S. P., Reddy, H., Cairano, Mond and Cohen, P. Specificity and mechanism of action of some commonly used protein kinase inhibitors. Biochem J, 351, 95-105, 2000.

39. Ponchel, F., Toomes, C., Bransfield, K., Leong, F. T., Douglas, S. H., Field, S. L., Bell, S. M., Combaret, V., Puisieux, A., Mighell, A. J., Robinson, P. A., Inglehearn, C. F., Isaacs, J. D and Markham, A. F. Real-time PCR based on SYBR-Green I fluorescence: an alternative to the TaqMan assay for a relative quantification of gene rearrangements, gene amplifications and micro gene deletions. BMC Biotechnol, 3, 18, 2003.

40. El-Tanani, M. K., Barraclough, R., Wilkinson, M. C and Rudland, P. S. Regulatory region of metastasis-inducing DNA is the binding site for T cell factor-4. Oncogene, 20, 1793-7, 2001.

41. Margalit, D. N., Romberg, L., Mets, R. B., Hebert, A. M., Mitchison, T. J., Kirschner, M. W and RayChaudhuri, D. Targeting cell division: small-molecule inhibitors of FtsZ GTPase perturb cytokinetic ring assembly and induce bacterial lethality. Proc Natl Acad Sci USA, 101, 11821-6, 2004.

42. Sakata, H., Stahl, S. J., Taylor, W. G., Rosenberg, J. M., Sakaguchi, K., Wingfield, P. T and Rubin, J. S. Heparin binding and oligomerization of hepatocyte growth factor/scatter factor isoforms. Heparan sulfate glycosaminoglycan requirement for Met binding and signaling. J Biol Chem, 272, 9457-63, 1997.

43. Sarbassov, D. D., Guertin, D. A., Ali, S. M and Sabatini, D. M. Phosphorylation and regulation of Akt/PKB by the rictor-mTOR complex. Science, 307, 1098-101, 2005.

44. Wang, D., Li, Z., Messing, E. M and Wu, G. Activation of Ras/Erk pathway by a novel MET-interacting protein Ran-BPM. J Biol Chem, 277, 36216-22, 2002

The invention claimed is:

1. A method of determining whether a tumour cell is likely to have an increased incidence of metastasis comprising the steps:
   determining the level of a marker in a tumour cell from a sample, wherein the marker is at least one member of the group comprising the RAN polypeptide of SEQ ID NO 1, the RAN Binding Protein 1 of SEQ ID NO 3, an active fragment of said RAN polypeptide, an active fragment of said RAN Binding Protein 1, a nucleic acid sequence encoding said RAN polypeptide, a nucleic acid sequence encoding said RAN Binding Protein 1, a nucleic acid sequence encoding an active fragment of said RAN polypeptide, and a nucleic acid sequence encoding an active fragment of said RAN Binding Protein 1 and
   comparing the level of the marker detected with the level determined for the marker in a non-invasive and/or non-metastatic tumour cell,
   wherein an increase in the level of the marker in the tumour cell from the sample is indicative that the tumour cell is likely to have an increased incidence of metastasis.

2. A method for monitoring a tumour to determine the invasive and/or metastatic potential of said tumour, the method comprising the steps of:
   a) detecting in a tumour cell at a first time point, the level of a marker, wherein the marker is at least one member of the group comprising the RAN polypeptide of SEQ ID NO 1, the RAN Binding Protein 1 of SEQ ID NO 3, an active fragment of said RAN polypeptide, an active fragment of said RAN Binding Protein 1, a nucleic acid sequence encoding said RAN polypeptide, a nucleic acid sequence encoding said RAN Binding Protein 1, a nucleic acid sequence encoding an active fragment of said RAN polypeptide, and a nucleic acid sequence encoding an active fragment of said RAN Binding Protein 1,
   b) repeating step a) at a subsequent point in time; and
   c) comparing the level of a marker in steps a) and b) wherein an increase in the level of marker from a first time point to a subsequent time point is indicative that the tumour cell is gaining invasive and/or metastatic potential.

3. The method as claimed in claim 1 wherein the level of the marker is determined by detecting the binding of an antibody, antibody derivative or antibody fragment with binding specificity to at least one of the RAN polypeptide of SEQ ID NO 1, the RAN Binding Protein 1 of SEQ ID NO 3, an active fragment of said RAN polypeptide, and an active fragment of said RAN Binding Protein 1.

4. The method as claimed in claim 2 wherein the level of the marker is determined by detecting the binding of an antibody, antibody derivative or antibody fragment with binding specificity to at least one of the RAN polypeptide of SEQ ID NO 1, the RAN Binding Protein 1 of SEQ ID NO 3, an active fragment of said RAN polypeptide, and an active fragment of said RAN Binding Protein 1.

* * * * *

SEQUENCE LISTING

<160> NUMBER OF SEQ ID NOS: 26

<210> SEQ ID NO 1
<211> LENGTH: 216
<212> TYPE: PRT
<213> ORGANISM: Homo sapiens

<400> SEQUENCE: 1

```
Met Ala Ala Gln Gly Glu Pro Gln Val Gln Phe Lys Leu Val Leu Val
1               5                   10                  15

Gly Asp Gly Gly Thr Gly Lys Thr Thr Phe Val Lys Arg His Leu Thr
            20                  25                  30

Gly Glu Phe Glu Lys Lys Tyr Val Ala Thr Leu Gly Val Glu Val His
        35                  40                  45

Pro Leu Val Phe His Thr Asn Arg Gly Pro Ile Lys Phe Asn Val Trp
    50                  55                  60

Asp Thr Ala Gly Gln Glu Lys Phe Gly Gly Leu Arg Asp Gly Tyr Tyr
65                  70                  75                  80

Ile Gln Ala Gln Cys Ala Ile Ile Met Phe Asp Val Thr Ser Arg Val
                85                  90                  95

Thr Tyr Lys Asn Val Pro Asn Trp His Arg Asp Leu Val Arg Val Cys
            100                 105                 110

Glu Asn Ile Pro Ile Val Leu Cys Gly Asn Lys Val Asp Ile Lys Asp
        115                 120                 125

Arg Lys Val Lys Ala Lys Ser Ile Val Phe His Arg Lys Lys Asn Leu
    130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190

Leu Ala Ala Gln Tyr Glu His Asp Leu Glu Val Ala Gln Thr Thr Ala
        195                 200                 205

Leu Pro Asp Glu Asp Asp Asp Leu
    210                 215
```

<210> SEQ ID NO 2
<211> LENGTH: 1656
<212> TYPE: DNA
<213> ORGANISM: Homo sapiens

<400> SEQUENCE: 2

```
cgccctgct  ctcgcgccgg  cgtcggctgc  gtctccggcg  tttgaattgc  gcttccgcca     60
tctttccagc  ctcagtcgga  cgggcgcgga  ggcgcttctg  gaaggaacgc  gcgatggct   120 gcgcagggag  agccccaggt  ccagttcaaa  cttgtattgg  ttggtgatgg  tggtactgga   180
aaaacgacct  tcgtgaaacg  tcatttgact  ggtgaatttg  agaagaagta  tgtagccacc   240
ttgggtgttg  aggttcatcc  cctagtgttc  cacaccaaca  gaggacctat  taagttcaat   300
gtatgggaca  cagccggcca  ggagaaattc  ggtggactga  gagatggcta  ttatatccaa   360
gcccagtgtg  ccatcataat  gtttgatgta  acatcgagag  ttacttacaa  gaatgtgcct   420
```

```
aactggcata gagatctggt acgagtgtgt gaaaacatcc ccattgtgtt gtgtggcaac    480
aaagtggata ttaaggacag gaaagtgaag gcgaaatcca ttgtcttcca ccgaaagaag    540
aatcttcagt actacgacat ttctgccaaa agtaactaca actttgaaaa gcccttcctc    600
tggcttgcta ggaagctcat ggagaccct aacttggaat tgttgccat gcctgctctc     660 gccccaccag aagttgtcat ggacccagct ttggcagcac agtatgagca cgacttagag    720
gttgctcaga caactgctct cccggatgag atgatgacc tgtgagaatg aagctggagc     780
ccagcgtcag aagtctagtt ttataggcag ctgtcctgtg atgtcagcgg tgcagcgtgt    840
gtgccacctc attattatct agctaagcgg aacatgtgct ttatctgtgg gatgctgaag    900
gagatgagtg ggcttcggag tgaatgtggc agtttaaaaa ataacttcat tgtttggacc    960
tgcatattta gctgtttgga cgcagttgat tccttgagtt tcatatataa gactgctgca    1020
gtcacatcac aatattcagt ggtgaaatct tgtttgttac tgtcattccc attccttttc    1080
tttagaatca gaataaagtt gtatttcaaa tatctaagca agtgaactca tcccttgttt    1140
ataaatagca tttggaaacc actaaagtag ggaagtttta tgccatgtta atatttgaat    1200
tgccttgctt ttatcactta atttgaaatc tattgggtta atttctccct atgtttattt    1260
ttgtacattt gagccatgtc acacaaactg atgatgacag gtcagcagta ttctatttgg    1320
ttagaagggt tacatggtgt aaatattagt gcagttaagc taaagcagtg tttgctccac    1380
cttcatattg gctaggtagg gtcacctagg gaagcacttg ctcaaaatct gtgacctgtc    1440
agaataaaaa tgtggtttgt acatatcaaa tagatatttt aagggtaata ttttctttta    1500
tggcaaaagt aatcatgttt taatgtagaa cctcaaacag gatggaacat cagtggatgg    1560
caggaggttg ggaattcttg ctgttaaaaa taattacaaa ttttgcactt tttgtttgaa    1620
tgttagatgc ttagtgtgaa gttgatacgc aagccg                              1656
```

<210> SEQ ID NO 3
<211> LENGTH: 201
<212> TYPE: PRT
<213> ORGANISM: Homo sapiens

<400> SEQUENCE: 3

```
Met Ala Ala Ala Lys Asp Thr His Glu Asp His Asp Thr Ser Thr Glu
1               5                   10                  15

Asn Thr Asp Glu Ser Asn His Asp Pro Gln Phe Glu Pro Ile Val Ser
            20                  25                  30

Leu Pro Glu Gln Glu Ile Lys Thr Leu Glu Glu Asp Glu Glu Glu Leu
        35                  40                  45

Phe Lys Met Arg Ala Lys Leu Phe Arg Phe Ala Ser Glu Asn Asp Leu
    50                  55                  60

Pro Glu Trp Lys Glu Arg Gly Thr Gly Asp Val Lys Leu Leu Lys His
65                  70                  75                  80

Lys Glu Lys Gly Ala Ile Arg Leu Leu Met Arg Arg Asp Lys Thr Leu
                85                  90                  95

Lys Ile Cys Ala Asn His Tyr Ile Thr Pro Met Met Glu Leu Lys Pro
            100                 105                 110

Asn Ala Gly Ser Asp Arg Ala Trp Val Trp Asn Thr His Ala Asp Phe
        115                 120                 125

Ala Asp Glu Cys Pro Lys Pro Glu Leu Leu Ala Ile Arg Phe Leu Asn
    130                 135                 140

Ala Glu Asn Ala Gln Lys Phe Lys Thr Lys Phe Glu Glu Cys Arg Lys
145                 150                 155                 160
```

Glu Ile Glu Glu Arg Glu Lys Lys Ala Gly Ser Gly Lys Asn Asp His
            165                 170                 175

Ala Glu Lys Val Ala Glu Lys Leu Glu Ala Leu Ser Val Lys Glu Glu
        180                 185                 190

Thr Lys Glu Asp Ala Glu Glu Lys Gln
        195                 200

<210> SEQ ID NO 4
<211> LENGTH: 884
<212> TYPE: DNA
<213> ORGANISM: Homo sapiens

<400> SEQUENCE: 4
cgaggttcgg gtcgtggggc ggagggaaga gcgggcgggc gggaggcgcc ggcgccagac      60
gcggagggaa ggagctacga gtagccgccg agaggccgcg gagccagcga cgaccgaccc     120
agccgagccg ccgccgccgc cgcgccccca tggcggccgc caaggacact catgaggacc     180
atgatacttc cactgagaat acagacgagt ccaaccatga ccctcagttt gagccaatag     240
tttctcttcc tgagcaagaa attaaaacac tggaagaaga tgaagaggaa cttttaaaa      300 tgcgggcaaa actgttccga tttgcctctg agaacgatct cccagaatgg aaggagcgag     360
gcactggtga cgtcaagctc ctgaagcaca aggagaaagg ggccatccgc tcctcatgc      420 ggagggacaa gaccctgaag atctgtgcca accactacat cacgccgatg atggagctga     480
agcccaacgc aggtagcgac cgtgcctggg tctggaacac ccacgctgac ttcgccgacg     540
agtgccccaa gccagagctg ctggccatcc gcttcctgaa tgctgagaat gcacagaaat     600
tcaaaacaaa gtttgaagaa tgcaggaaag agatcgaaga gagagaaaag aaagcaggat     660
caggcaaaaa tgatcatgcc gaaaaagtgg cggaaaagct agaagctctc tcggtgaagg     720
aggagaccaa ggaggatgct gaggagaagc aataaatcgt cttattttat tttcttttcc     780
tctctttcct ttcctttttt taaaaaattt taccctgccc ctcttttcg gtttgttttt      840 attctttcat ttttacaagg gacgttatat aaagaactga actc                      884

<210> SEQ ID NO 5
<211> LENGTH: 25
<212> TYPE: DNA
<213> ORGANISM: Artificial
<220> FEATURE:
<223> OTHER INFORMATION: siRNA

<400> SEQUENCE: 5
aaaaacgacc ttcgtgaaac gtcat                                            25

<210> SEQ ID NO 6
<211> LENGTH: 22
<212> TYPE: DNA
<213> ORGANISM: Artificial
<220> FEATURE:
<223> OTHER INFORMATION: siRNA

<400> SEQUENCE: 6
aagcccagtg tgccatcata at                                               22

<210> SEQ ID NO 7
<211> LENGTH: 21
<212> TYPE: DNA
<213> ORGANISM: Artificial
<220> FEATURE:
<223> OTHER INFORMATION: siRNA

<400> SEQUENCE: 7
aagtatgtag ccaccttggg t				21

<210> SEQ ID NO 8
<211> LENGTH: 19
<212> TYPE: DNA
<213> ORGANISM: Artificial
<220> FEATURE:
<223> OTHER INFORMATION: SiRNA

<400> SEQUENCE: 8
tacagacgag tccaaccat				19

<210> SEQ ID NO 9
<211> LENGTH: 19
<212> TYPE: DNA
<213> ORGANISM: Artificial
<220> FEATURE:
<223> OTHER INFORMATION: siRNA

<400> SEQUENCE: 9
ccactacatc acgccgatg				19

<210> SEQ ID NO 10
<211> LENGTH: 19
<212> TYPE: DNA
<213> ORGANISM: Artificial
<220> FEATURE:
<223> OTHER INFORMATION: siRNA

<400> SEQUENCE: 10
ggacactcat gaggaccat				19

<210> SEQ ID NO 11
<211> LENGTH: 35
<212> TYPE: DNA
<213> ORGANISM: Artificial
<220> FEATURE:
<223> OTHER INFORMATION: oligonucleotide

<400> SEQUENCE: 11
aacttgtatt ggttggtgat gttggtactg gaaaa				35

<210> SEQ ID NO 12
<211> LENGTH: 35
<212> TYPE: DNA
<213> ORGANISM: Artificial
<220> FEATURE:
<223> OTHER INFORMATION: oligonucleotide

<400> SEQUENCE: 12
ttttccagta ccaacatcac caaccaatac aagtt				35

<210> SEQ ID NO 13
<211> LENGTH: 36
<212> TYPE: DNA
<213> ORGANISM: Artificial
<220> FEATURE:
<223> OTHER INFORMATION: oligonucleotide

<400> SEQUENCE: 13
gggacacagc cggcctggag aaattcggtg gactga				36

```
<210> SEQ ID NO 14
<211> LENGTH: 36
<212> TYPE: DNA
<213> ORGANISM: Artificial
<220> FEATURE:
<223> OTHER INFORMATION: oligonucleotide

<400> SEQUENCE: 14
tcagtccacc gaatttctcc aggccggctg tgtccc                              36

<210> SEQ ID NO 15
<211> LENGTH: 17
<212> TYPE: DNA
<213> ORGANISM: Artificial
<220> FEATURE:
<223> OTHER INFORMATION: oligonucleotide

<400> SEQUENCE: 15
gatcgcggac gggttgt                                                    17

<210> SEQ ID NO 16
<211> LENGTH: 18
<212> TYPE: DNA
<213> ORGANISM: Artificial
<220> FEATURE:
<223> OTHER INFORMATION: oligonucleotide

<400> SEQUENCE: 16
ttcagcggag gcatttcc                                                   18

<210> SEQ ID NO 17
<211> LENGTH: 22
<212> TYPE: DNA
<213> ORGANISM: Artificial
<220> FEATURE:
<223> OTHER INFORMATION: oligonucleotide

<400> SEQUENCE: 17
gctgctgcct accctagtct ca                                              22

<210> SEQ ID NO 18
<211> LENGTH: 21
<212> TYPE: DNA
<213> ORGANISM: Artificial
<220> FEATURE:
<223> OTHER INFORMATION: oligonucleotide

<400> SEQUENCE: 18
gctgctcgtg tctggaattg t                                               21

<210> SEQ ID NO 19
<211> LENGTH: 26
<212> TYPE: DNA
<213> ORGANISM: Artificial
<220> FEATURE:
<223> OTHER INFORMATION: oligonucleotide

<400> SEQUENCE: 19
cagggtagtt tagttgaggt tgacag                                          26

<210> SEQ ID NO 20
<211> LENGTH: 25
<212> TYPE: DNA
<213> ORGANISM: Artificial
<220> FEATURE:
<223> OTHER INFORMATION: oligonucleotide
```

```
<400> SEQUENCE: 20
ctatactggt ggtcagtgcc aaagt                                          25

<210> SEQ ID NO 21
<211> LENGTH: 18
<212> TYPE: DNA
<213> ORGANISM: Artificial
<220> FEATURE:
<223> OTHER INFORMATION: oligonucleotide

<400> SEQUENCE: 21
tactggaaaa acgacctt                                                  18

<210> SEQ ID NO 22
<211> LENGTH: 18
<212> TYPE: DNA
<213> ORGANISM: Artificial
<220> FEATURE:
<223> OTHER INFORMATION: oligonucleotide

<400> SEQUENCE: 22
tcccatacat tgaactta                                                  18

<210> SEQ ID NO 23
<211> LENGTH: 20
<212> TYPE: DNA
<213> ORGANISM: Artificial
<220> FEATURE:
<223> OTHER INFORMATION: oligonucleotide

<400> SEQUENCE: 23
gtaacccgtt gaaccccatt                                                20

<210> SEQ ID NO 24
<211> LENGTH: 20
<212> TYPE: DNA
<213> ORGANISM: Artificial
<220> FEATURE:
<223> OTHER INFORMATION: oligonucleotide

<400> SEQUENCE: 24
ccatccaatc ggtagtagcg                                                20

<210> SEQ ID NO 25
<211> LENGTH: 18
<212> TYPE: DNA
<213> ORGANISM: Artificial
<220> FEATURE:
<223> OTHER INFORMATION: oligonucleotide

<400> SEQUENCE: 25
atggctgcgc agggagag                                                  18

<210> SEQ ID NO 26
<211> LENGTH: 18
<212> TYPE: DNA
<213> ORGANISM: Artificial
<220> FEATURE:
<223> OTHER INFORMATION: oligonucleotide

<400> SEQUENCE: 26
ggggcgagag caggcatg                                                  18
```